United States Patent
Sando et al.

(10) Patent No.: US 10,012,644 B2
(45) Date of Patent: Jul. 3, 2018

(54) SENSOR, DETECTION METHOD, DETECTION SYSTEM, AND DETECTION DEVICE

(71) Applicants: KYUSHU UNIVERSITY, NATIONAL UNIVERSITY CORPORATION, Fukuoka-shi, Fukuoka (JP); KYOCERA Corporation, Kyoto-shi, Kyoto (JP)

(72) Inventors: Shinsuke Sando, Fukuoka (JP); Hideharu Kurioka, Kizugawa (JP)

(73) Assignees: KYOCERA Corporation, Kyoto (JP); Kyushu University, National University Corporation, Fukuoka (JP)

( * ) Notice: Subject to any disclaimer, the term of this patent is extended or adjusted under 35 U.S.C. 154(b) by 440 days.

(21) Appl. No.: 14/389,745

(22) PCT Filed: Mar. 29, 2013

(86) PCT No.: PCT/JP2013/059658
§ 371 (c)(1),
(2) Date: Sep. 30, 2014

(87) PCT Pub. No.: WO2013/147217
PCT Pub. Date: Oct. 3, 2013

(65) Prior Publication Data
US 2015/0065394 A1 Mar. 5, 2015

(30) Foreign Application Priority Data
Mar. 30, 2012 (JP) .................. 2012-080812

(51) Int. Cl.
*G01N 33/543* (2006.01)
*G01N 29/02* (2006.01)
*G01N 29/22* (2006.01)

(52) U.S. Cl.
CPC ..... *G01N 33/54373* (2013.01); *G01N 29/022* (2013.01); *G01N 29/222* (2013.01);
(Continued)

(58) Field of Classification Search
CPC ....... G01N 33/54373; G01N 33/54306; G01N 29/022; G01N 29/222
See application file for complete search history.

(56) References Cited

U.S. PATENT DOCUMENTS 5,283,037 A  2/1994  Baer et al.
6,242,246 B1  6/2001  Gold et al.
(Continued)

FOREIGN PATENT DOCUMENTS

JP  H05-240762 A  9/1993
JP  2002-508191 A  3/2002
(Continued)

OTHER PUBLICATIONS

International Search Report dated Jul. 2, 2013, issued for International Application No. PCT/JP2013/059658.
(Continued)

*Primary Examiner* — Melanie Yu Brown
(74) *Attorney, Agent, or Firm* — Procopio Cory Hargreaves and Savitch LLP

(57) ABSTRACT

In an aspect, a sensor includes a combining portion that combines with a second substance having a molecular weight larger than a molecular weight of a first substance. Further, in an aspect, the sensor includes a substrate including a surface on which the combining portion is disposed. The combining portion detects whether or not the first substance is included in an analyte that has come into contact with both an aptamer and the second substance. The aptamer includes a first combining part for the first substance and a second combining part for the second substance
(Continued)

and is combined with either of the first substance and the second substance.

16 Claims, 22 Drawing Sheets

(52) U.S. Cl.
CPC .............. *G01N 33/54306* (2013.01); *G01N 2291/0255* (2013.01); *G01N 2291/0256* (2013.01); *G01N 2291/0423* (2013.01)

(56) References Cited

U.S. PATENT DOCUMENTS

| | | | |
|---|---|---|---|
| 6,294,391 B1* | 9/2001 | Badley | G01N 33/54373 310/311 |
| 6,458,543 B1 | 10/2002 | Gold et al. | |
| 6,503,715 B1 | 1/2003 | Gold et al. | |
| 6,544,776 B1 | 4/2003 | Gold et al. | |
| 7,709,192 B2 | 5/2010 | Gold et al. | |
| 7,807,351 B2 | 10/2010 | Sode et al. | |
| 8,247,197 B2 | 8/2012 | Sode et al. | |
| 2004/0072208 A1* | 4/2004 | Warthoe | C12Q 1/6825 435/6.11 |
| 2005/0142582 A1* | 6/2005 | Doyle | C12N 15/115 435/6.12 |
| 2006/0049047 A1* | 3/2006 | Sato | G01N 27/3272 204/403.01 |
| 2008/0287666 A1 | 11/2008 | Watanabe et al. | |
| 2009/0111094 A1 | 4/2009 | Storhoff et al. | |
| 2010/0282617 A1 | 11/2010 | Rothberg et al. | |
| 2010/0317128 A1 | 12/2010 | Harada et al. | |
| 2011/0053285 A1* | 3/2011 | Jeon | G01N 21/4738 436/164 |
| 2012/0129248 A1* | 5/2012 | Chee | C12Q 1/34 435/287.1 |
| 2013/0157279 A1 | 6/2013 | Takoh | |
| 2015/0065394 A1 | 3/2015 | Sando et al. | |

FOREIGN PATENT DOCUMENTS

| | | |
|---|---|---|
| JP | 2005-249491 A | 9/2005 |
| JP | 2006-184011 A | 7/2006 |
| JP | 2008-278837 A | 11/2008 |
| JP | 2009-505106 A | 2/2009 |
| JP | 2009-201406 A | 9/2009 |
| JP | 2010-239477 A | 10/2010 |
| JP | 2011-525990 A | 9/2011 |
| JP | 5566543 B2 | 8/2014 |
| WO | 2005-049826 A1 | 6/2005 |
| WO | 2012-029224 A1 | 3/2012 |

OTHER PUBLICATIONS

Office Action dated Jul. 18, 2017 issued in counterpart Japanese Application No. 2014-046902.

* cited by examiner

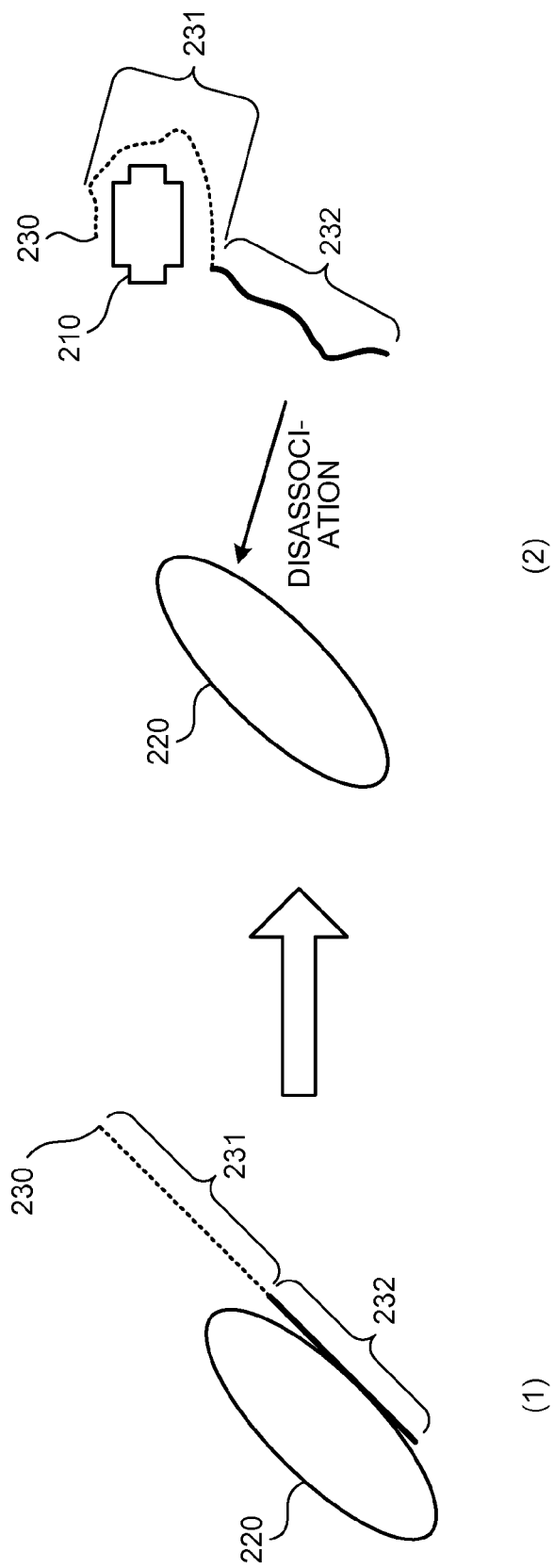

FIG.14
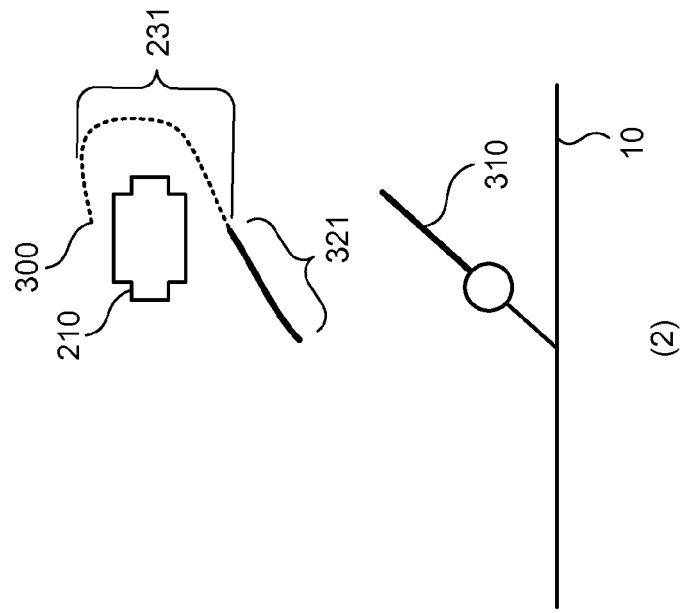
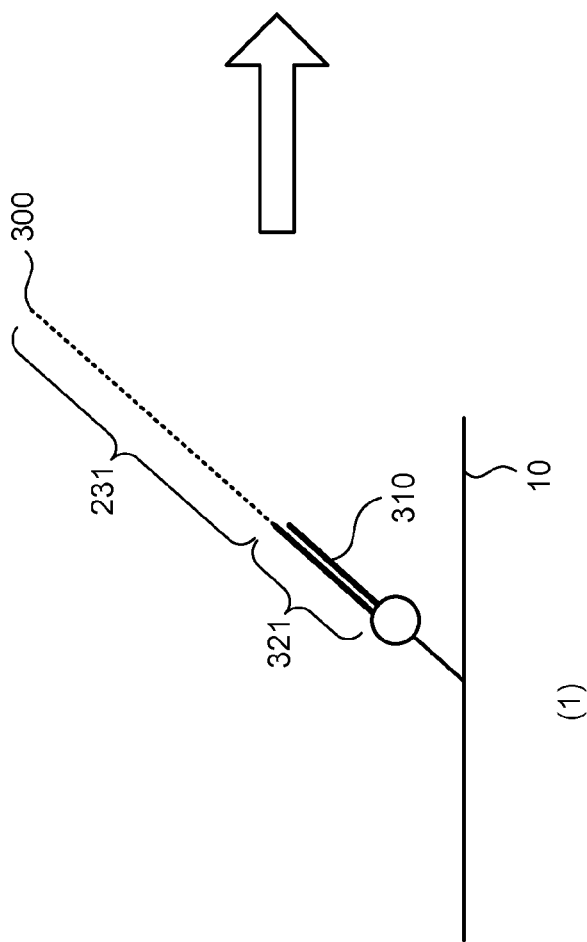

FIG.15

5'-ACCTGGGGAGTATTGCGGAGGAAGGT-3'
3'-CCTCCTTCCATTTTTTTTTTTTTTTTTTTTTTTTTT-5'

Sensorgrams of DNA immobilization

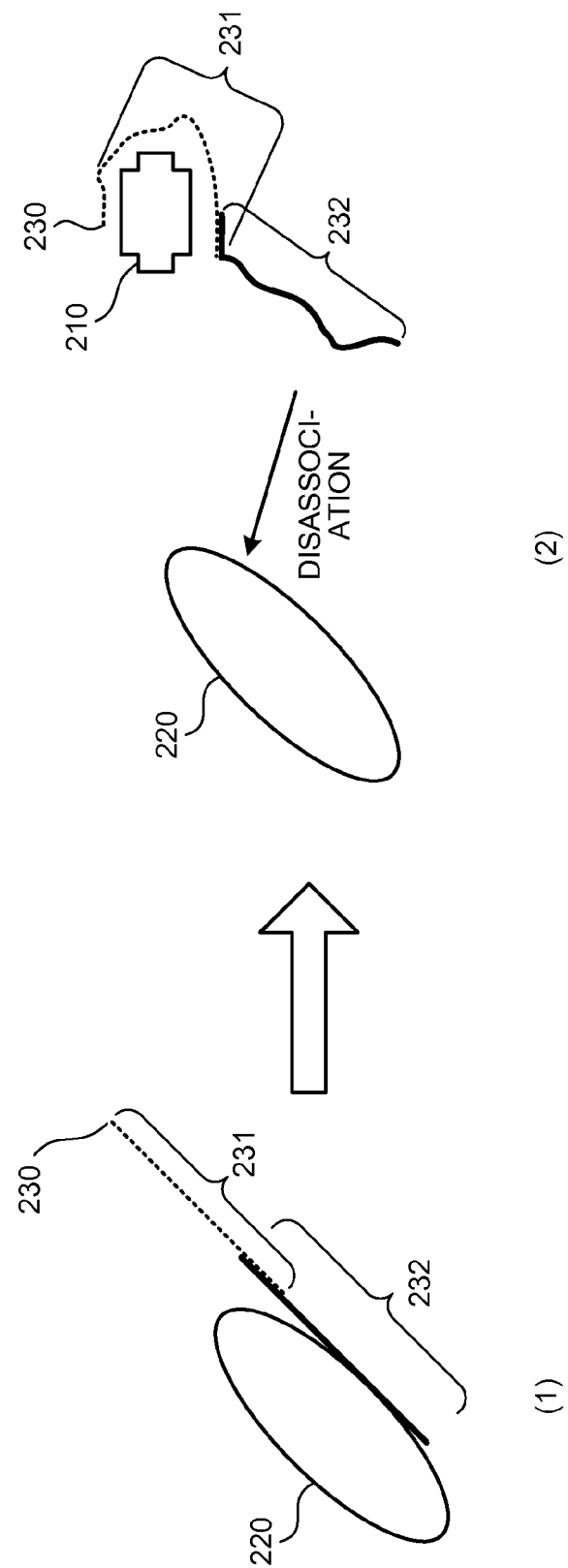

US 10,012,644 B2

SENSOR, DETECTION METHOD, DETECTION SYSTEM, AND DETECTION DEVICE

CROSS-REFERENCE TO RELATED APPLICATIONS

This application is national stage application of International Application No. PCT/JP2013/059658, filed on Mar. 29, 2013, which designates the United States, incorporated herein by reference, and which claims the benefit of priority from Japanese Patent Application No. 2012-080812, filed on Mar. 30, 2012, the entire contents of which are incorporated herein by reference.

FIELD

The present invention relates to a sensor, a detection method, a detection system, and a detection device.

BACKGROUND

In the past, there is a detection technique of detecting a state change of a substrate surface. For example, there is a sensor of measuring a property or a component of an analyte solution using a surface acoustic wave. Further, for example, there is a surface plasmon resonance (SPR) measuring device.

Further, there is a measurement technique using a complex including an aptamer part that is combined with thrombin and inhibits enzyme activity of thrombin and a probe part that is combined with a target molecule. In the measurement technique using a complex, for example, when a target molecule is combined with a probe part, thrombin is not combined with an aptamer part, and thrombin shows activity. In the measurement technique using a complex, the presence of a target molecule is detected by measuring enzyme activity of thrombin.

Further, there is a sensor in which one or more specific nucleic acid ligands are attached to a substrate. Further, there is also a sensor in which a measuring electrode is coated with an enzyme or the like, and a sensor absorbs an analyte solution using a capillary phenomenon.

CITATION LIST

Patent Literature

Patent Literature 1: Japanese Patent Application Laid-open No. H05-240762
Patent Literature 2: Japanese Patent Application Laid-open No. 2006-184011
Patent Literature 3: Japanese Patent Application Laid-open No. 2010-239477
Patent Literature 4: Japanese Patent Application Laid-open No. 2005-249491
Patent Literature 5: International Publication Pamphlet No. WO 2005/049826
Patent Literature 6: Japanese National Publication of International Patent Application No. 2002-508191
Patent Literature 7: Japanese National Publication of International Patent Application No. 2009-505106

SUMMARY

Technical Problem

However, in the detection technique of the related art of detecting the state change of the substrate surface, there is a problem in that detection sensitivity for small molecules having a small molecular weight is bad, and thus it is difficult to detect small molecules.

The technology disclosed herein was made in light of the foregoing, and it is an object of the technology to provide a sensor, a detection method, a detection system, and a detection device, which are capable of detecting small molecules.

Solution to Problem

A sensor disclosed herein includes a combining portion that combines with a second substance having a molecular weight larger than a molecular weight of a first substance. Further, according to one aspect, the sensor includes a substrate including a surface on which the combining portion is disposed for detecting whether or not the first substance is included in an analyte having come into contact with both an aptamer and the second substance, the aptamer including a first combining part for the first substance and a second combining part for the second substance and being combined with either of the first substance and the second substance.

Advantageous Effects of Invention

According to an aspect of the detection method according to the disclosure, an effect capable of detecting small molecule is obtained.

BRIEF DESCRIPTION OF DRAWINGS

FIG. 12 is a diagram for describing an example of an embodiment of an aptamer according to the disclosure.
FIG. 14 is a diagram for describing another embodiment of a sensor.

FIG. 15 is a diagram for describing a base sequence relation between an ATP aptamer and a complementary strand DNA "A."

FIG. 24 is a diagram for describing an example of an embodiment of an aptamer according to the disclosure.

DESCRIPTION OF EMBODIMENTS

Figure 1:
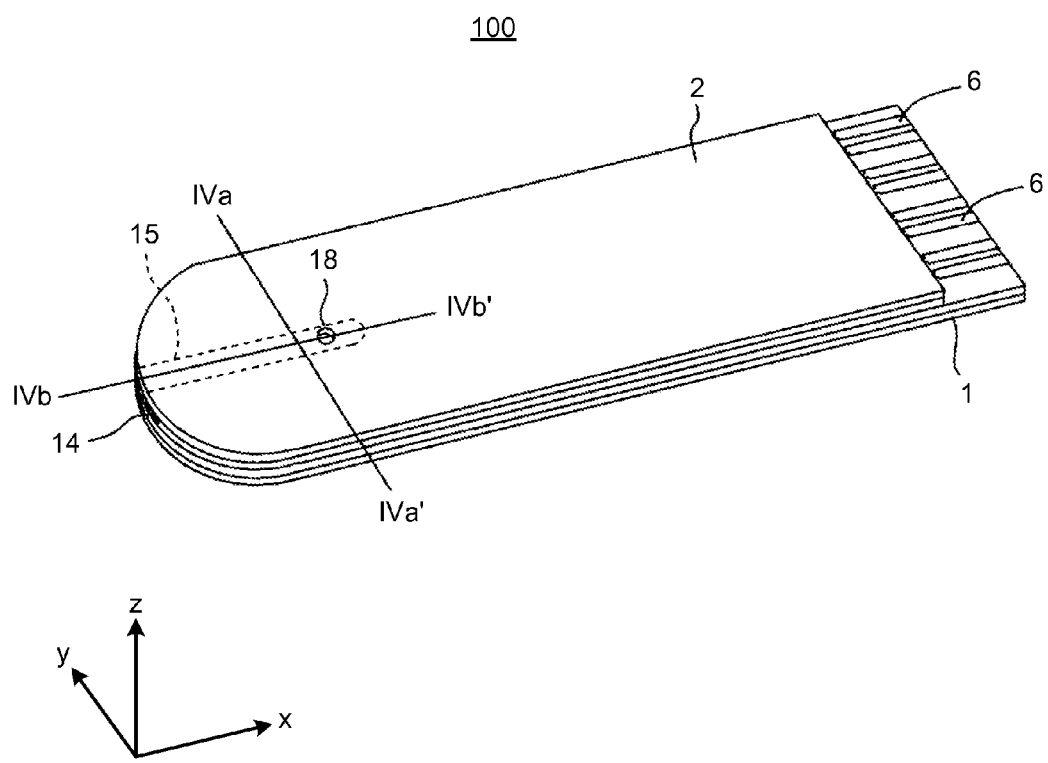
FIG. 1 is a perspective view of a sensor according to an embodiment of the present invention.

Detecting Portion of Sensor, Detection Method, Detection System, and Detection Device According to First Embodiment Hereinafter, embodiments of a sensor, a detection method, a detection system, and a detection device according to the disclosure will be described in detail with reference to the appended drawings. As will be described below in detail, a sensor, a detection method, a detection system, and a detection device according to the disclosure are capable of detecting a first substance by performing a comparison with a first substance and detecting a state change of a substrate surface caused by a substance having a large molecular weight. As a result, it is possible to detect a small molecule having a small molecular weight as well.

Hereinafter, a first substance serving as a detection target is also referred to as a "target substance." Further, when a numerical value range is indicated using "to," it is assumed to include an upper limit value and a lower limit value unless otherwise stated. For example, a numerical value range of "300 to 500" indicates that a lower limit is "300 or more," and an upper limit is "500 or less" unless otherwise stated.

Structure of Sensor

A sensor in which a detecting portion is mounted will be described before the details of a detecting portion of a sensor are described. The sensor according to the disclosure can be used in a detection technique of detecting a state change of a substrate surface. Examples of the sensor according to the disclosure include a measuring cell used for measurement by a surface plasmon resonance (SPR) device, a surface acoustic wave (SAW) sensor, and a quarts crystal microbalance (QCM) crystal sensor. Preferably, the sensor according to the disclosure is an SAW sensor. As the sensor is implemented as the SAW sensor, the sensor can be simply implemented in small size.

Hereinafter, an exemplary structure of the sensor according to the disclosure will be described in detail in connection with an example in which the sensor according to the disclosure is the SAW sensor. As will be described below in detail, in an example of an embodiment, a sensor 100 serving as the SAW sensor includes a first cover member 1 on which a substrate 10 is positioned and a second cover member 2 bonded to the first cover member 1. Further, in the sensor 100, at least one of the first cover member 1 and the second cover member 2 includes an inlet 14 through which an analyte flows in, and a flow channel 15 extending from the inlet 14 up to at least the surface of the substrate 10 is formed between the first cover member 1 and the second cover member 2.

In an example of an embodiment, for example, the sensor 100 includes the first cover member 1 on which a substrate 10 is positioned and the second cover member 2 bonded to the first cover member 1, and at least one of the first cover member 1 and the second cover member 2 includes an inlet 14 through which an analyte flows in and a groove portion 15 extending from the inlet 14 up to at least the surface of the substrate 10. For example, the first cover member 1 includes a concave portion accommodating at least a part of the substrate 10 on its upper surface, and the second cover member 2 includes the groove portion 15.

In an example of an embodiment, the sensor 100 serving as the SAW sensor further includes a first InterDigital Transducer (IDT) electrode that generates an acoustic wave to be propagated to a detecting portion (which will be described in detail later) positioned on the surface of the substrate 10. The sensor 100 further includes a second IDT electrode that is positioned on the surface of the substrate 10 and receives an acoustic wave passing through the detecting portion 13. The sensor 100 further includes a first bonding member that is bonded to the upper surface of the substrate 10 and has a first oscillation space hermetically-sealed between the first bonding member and the upper surface of the substrate 10. The sensor 100 further includes a second bonding member that is bonded to the upper surface of the substrate 10 and has a second oscillation space hermetically-sealed between the second bonding member and the upper surface of the substrate 10. Here, the first oscillation space is positioned above the first IDT electrode, and the second oscillation space is positioned above the second IDT electrode.

An exemplary configuration of the sensor 100 serving as the SAW sensor will be described in detail with reference to the appended drawings. In the drawings described below, the same components are denoted by the same reference numerals. Further, the size of each component, a distance between components, and the like are schematically illustrated and may be different from actual ones. In the sensor 100, any one direction may be regarded as an upper direction or a lower direction, and hereinafter, for the sake of convenience, an orthogonal coordinate system xyz is defined, and terms such as an upper surface, a lower surface, and the like are used under the assumption that a positive side in an z direction is an upper direction.

The sensor 100 is mainly configured with the first cover member 1, the second cover member 2, and a detecting element 3. The first cover member 1 includes a first substrate 1a and a second substrate 1b stacked on the first substrate 1a, and the second cover member 2 includes a third substrate 2a stacked on the second substrate 1b and a fourth substrate 2b stacked on the third substrate 2a. The detecting element 3 is an SAW element, and is mainly configured with the substrate 10, a first IDT electrode 11, a second IDT electrode 12, and the detecting portion 13.

The first cover member 1 is attached with the second cover member 2, and the detecting element 3 is accommodated between the first cover member 1 and the second cover member 2 attached to each other. As illustrated in cross-sectional views of FIGS. 4A and 4B, the first cover member 1 includes a concave portion 5 on its upper surface, and the detecting element 3 is arranged in the concave portion 5. The second cover member 2 includes the inlet 14 serving as an entrance of an analyte solution at its end portion in the longitudinal direction (the x direction), and includes the groove portion 15 extending from the inlet 14 toward a portion directly above the detecting element 3 as illustrated in FIG. 1. In FIG. 1, in order to indicate the position of the groove portion 15, the groove portion 15 is indicated by a dotted line. An analyte solution is a solution serving as a detection target as to whether or not a first substance 210 is included therein.

Figure 2:
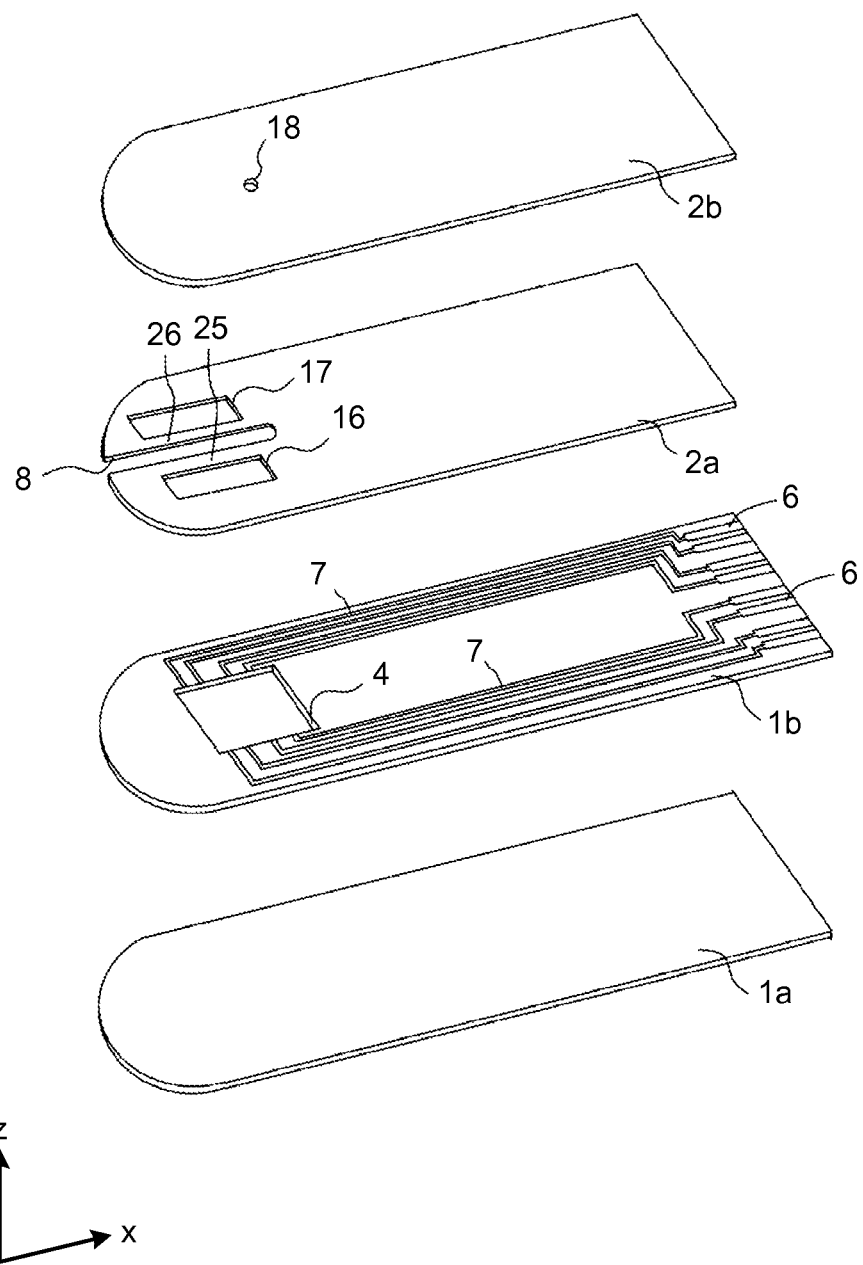
FIG. 2 is an exploded perspective view of a first cover member and a second cover member.

FIG. 2 is an exploded perspective view illustrating the first cover member 1 and the second cover member 2.

First, the first cover member 1 is described.

The first cover member 1 includes the first substrate 1a and the second substrate 1b stacked on the first substrate 1a as described above.

The first substrate 1a configuring the first cover member 1 has a flat plate shape, and has a thickness of, for example, 0.1 mm to 0.5 mm. The first substrate 1a has a roughly rectangular plane shape, but its one end in the longitudinal direction has an arc shape protruding outward. The length of the first substrate 1a in the x direction is, for example, 1 cm to 5 cm, and the length in the y direction is, for example, 1 cm to 3 cm.

The second substrate 1b is attached to the upper surface of the first substrate 1a. The second substrate 1b has a flat plate frame shape in which a concave portion forming through hole 4 is formed in a flat plate shaped plate, and has a thickness of, for example, 0.1 mm to 0.5 mm. An outer shape in a planar view has almost the same as that of the first substrate 1a, and the length in the x direction and the length in the y direction are almost the same as those of the first substrate 1a.

As the second substrate 1b in which the concave portion forming through hole 4 is formed is bonded to the first substrate 1a of the flat plate shape, the concave portion 5 is formed in the first cover member 1. In other words, the upper surface of the first substrate 1a positioned on the inside of the concave portion forming through hole 4 serves as the bottom surface of the concave portion 5, and the inner wall of the concave portion forming through hole 4 serves as the inner wall of the concave portion 5.

Further, terminals 6 and interconnections 7 extending from terminals 6 to the concave portion forming through hole 4 are formed on the upper surface of the second substrate 1b. The terminal 6 is formed on the other end portion of the upper surface of the second substrate 1b in the x direction. A portion in which the terminals 6 are formed is a portion that is actually inserted when the sensor 100 is inserted into an external measuring device (not illustrated), and electrically connected to an external measuring device via the terminals 6. The terminal 6 is electrically connected with the detecting element 3 via the interconnection 7 or the like. A signal output from the external measuring device is input to the sensor 100 through the terminal 6, and a signal output from the sensor 100 is input to the external measuring device through the terminal 6.

Next, the second cover member 2 will be described.

The second cover member 2 includes the third substrate 2a stacked on the second substrate 1b and the fourth substrate 2b stacked on the third substrate 2a as described above.

The second cover member 2 is bonded to the upper surface of the first cover member 1 configured with the first substrate 1a and the second substrate 1b. The second cover member 2 includes the third substrate 2a and the fourth substrate 2b.

The third substrate 2a is attached to the upper surface of the second substrate 1b. The third substrate 2a has a flat plate shape and has a thickness of, for example, 0.1 mm to 0.5 mm. The third substrate 2a has a roughly rectangular plane shape, but its one end in the longitudinal direction has an arc shape protruding outward, similarly to the first substrate 1a and the second substrate 1b. The length of the third substrate 2a in the x direction is slightly shorter than the length of the second substrate 1b in the x direction so that the terminal 6 formed on the second substrate 1b is exposed, and is, for example, 0.8 mm to 4.8 cm. The length in the y direction is, for example, 1 cm to 3 cm, similarly to the first substrate 1a and the second substrate 1b.

A notch 8 is formed in the third substrate 2a. The notch 8 is a part formed by cutting out the third substrate 2a from the apex of one end of the third substrate 2a having the arc shape toward the other end in the x direction. The notch 8 serves to form the groove portion 15. A first through hole 16 and a second through hole 17 passing through the third substrate 2a in the depthwise direction are formed on both sides of the notch 8 of the third substrate 2a. When the third substrate 2a is stacked on the second substrate 1b, a connection portion between the detecting element 3 and the interconnection 7 is positioned at the inside of the first through hole 16 and the second through hole 17. A portion between the first through hole 16 and the notch 8 of the third substrate 2a serves as a first partition portion 25 separating the groove portion 15 (which will be described later) from a space formed by the first through hole 16. Further, a portion between the second through hole 17 and the notch 8 of the third substrate 2a serves as a second partition portion 26 separating the groove portion 15 from a space formed by the second through hole 17.

The fourth substrate 2b is attached to the upper surface of the third substrate 2a. The fourth substrate 2b has a flat plate shape and has a thickness is, for example, 0.1 mm to 0.5 mm. An outer shape in a planar view is almost the same as that of the third substrate 2a, and the length in the x direction and the length in the y direction are almost the same as those of the third substrate 2a. As the fourth substrate 2b is bonded with the third substrate 2a in which the notch 8 is formed, the groove portion 15 is formed below the second cover member 2. In other words, the lower surface of the fourth substrate 2b positioned on the inside of the notch 8 serves as the bottom surface of the groove portion 15, and the inner wall of the notch 8 serves as the inner wall of the groove portion 15. The groove portion 15 extends from the inlet 14 up to at least a portion directly above the detecting portion 13, and has, for example, a rectangular cross-sectional shape.

A third through hole 18 passing through the fourth substrate 2b in the depthwise direction is formed in the fourth substrate 2b. The third through hole 18 is positioned above the end portion of the notch 8 when the fourth substrate 2b is stacked on the third substrate 2a. Thus, the end portion of the groove portion 15 is connected with the third through hole 18. The third through hole 18 is used to discharge, for example, air in the groove portion 15 to the outside.

The first substrate 1a, the second substrate 1b, the third substrate 2a, and the fourth substrate 2b are made of, for example, paper, plastic, celluloid, ceramics, or the like. The substrates can be formed of the same material. As all the substrates can be formed of the same material, the substances can have the same thermal expansion coefficient, and thus deformation caused by a thermal expansion coefficient difference between the substances is prevented. Further, the detecting portion 13 may be coated with biomaterials, but the detecting portion 13 may be likely to be altered due to external light such as ultraviolet light. In this case, it is desirable to use an opaque material having a light shielding property as materials of the first cover member 1 and the second cover member 2. Meanwhile, when the detecting portion 13 is hardly altered by external light, the second cover member 2 in which the groove portion 15 is formed may be formed of nearly a transparent material. In this case, it is possible to view a form of an analyte solution flowing in the flow channel 15.

Next, the detecting element 3 will be described.

Figure 5:
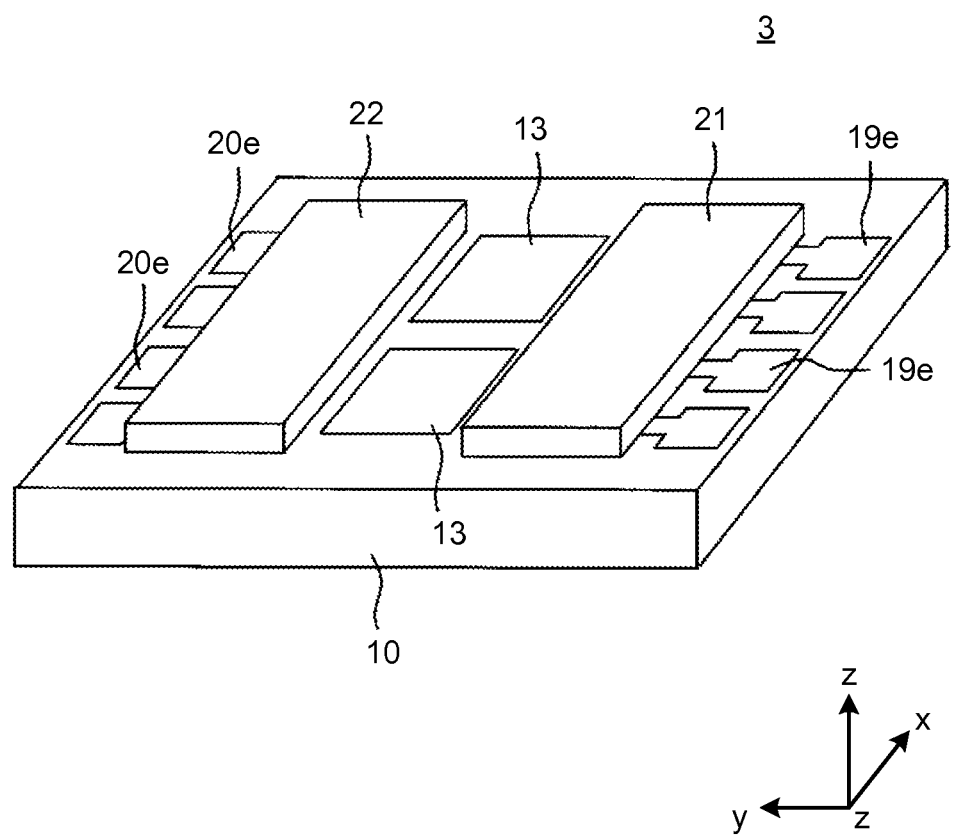
FIG. 5 is a perspective view of a detection element used in the sensor illustrated in FIG. 1.
Figure 6:
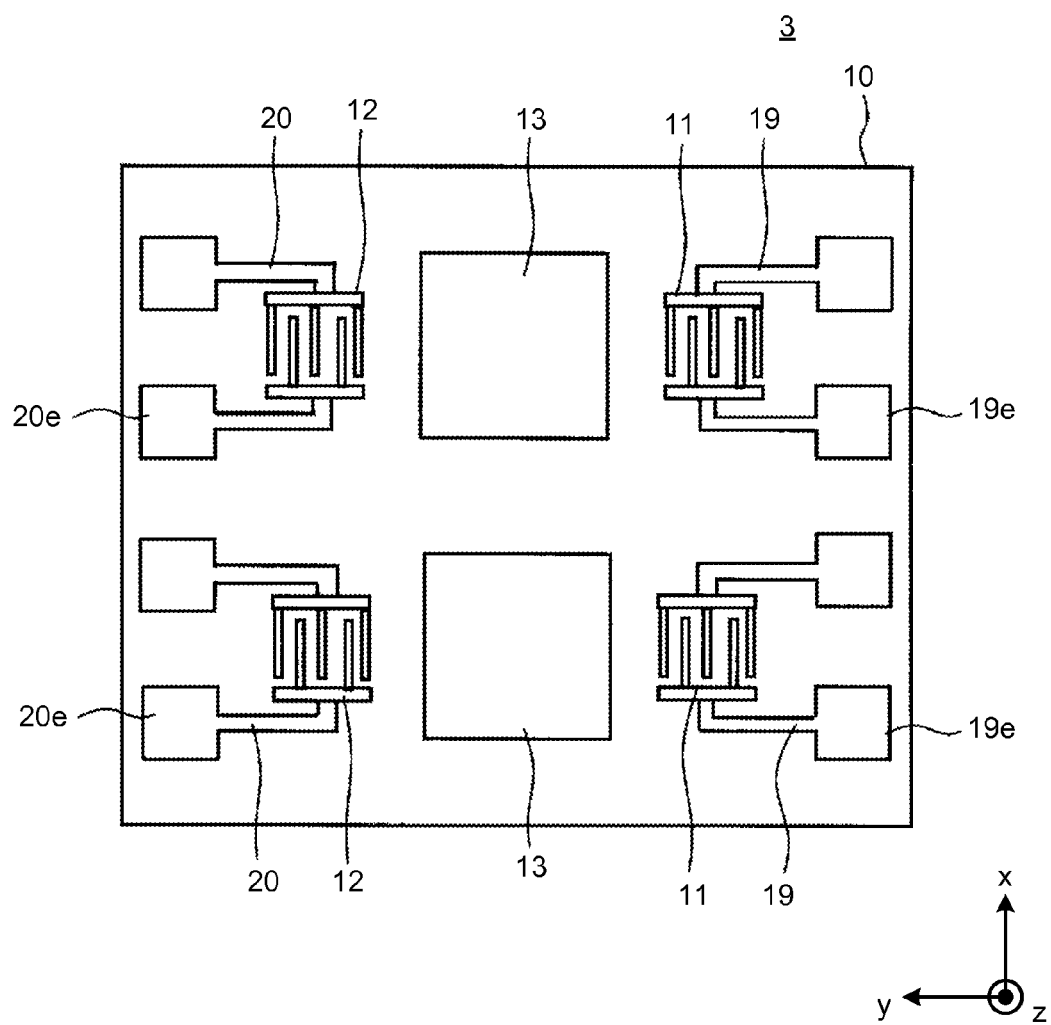
FIG. 6 is a plane view illustrating a state in which a first bonding member and a second bonding member of the detection element illustrated in FIG. 5 are taken off.

FIG. 5 is a perspective view illustrating the detecting element 3, and FIG. 6 is a plane view illustrating the detecting element 3 when a first bonding member 21 and a second bonding member 22 are taken out.

The detecting element 3 includes the substrate 10, the detecting portion 13 arranged on the upper surface of the substrate 10, the first IDT electrode 11, the second IDT electrode 12, a first extraction electrode 19, and a second extraction electrode 20.

For example, the substrate 10 is made of a single crystalline substrate having piezoelectricity such as a lithium tantalate ($LiTaO_3$) single crystal, a lithium niobate ($LiNbO_3$) single crystal, or a crystal. A plane shape and various kinds of dimensions of the substrate 10 may be appropriately set. For example, a thickness of the substrate 10 is 0.3 mm to 1 mm.

The first IDT electrode 11 includes a pair of comb electrodes as illustrated in FIG. 6. Each comb electrode includes two bus bars facing each other and a plurality of electrode fingers extending from each bus bar to the other bus bar side. A pair of comb electrodes is arranged such that a plurality of electrode fingers are engaged with one another. The second IDT electrode 12 has the same configuration as the first IDT electrode 11. The first IDT electrode 11 and the second IDT electrode 12 configure a transversal IDT electrode.

The first IDT electrode 11 generates a certain SAW, and the second IDT electrode 12 receives the SAW generated by the first IDT electrode 11. The first IDT electrode 11 and the second IDT electrode 12 are arranged in the same straight line form so that the SAW generated by the first IDT electrode 11 can be received by the second IDT electrode 12. A frequency characteristic can be designed using the number of electrode fingers of the first IDT electrode 11 and the second IDT electrode 12, a distance between neighboring electrode fingers, a cross width of an electrode finger, and the like as parameters. As an SAW excited by an IDT electrode, there are waves of various oscillation modes, but in the detecting element 3, for example, an oscillation mode of a transversal wave called an SH wave is used.

Further, an elastic member for suppressing reflection of an SAW may be installed outside the first IDT electrode 11 and the second IDT electrode 12 in an SAW propagation direction (the y direction). For example, a frequency of an SAW can be set within a range from several megahertz (MHz) to several gigahertz (GHz). Here, when a frequency of an SAW is set to hundreds of MHz to 2 GHz, it is practical, and downsizing of the detecting element 3 and downsizing of the sensor 100 can be implemented.

The first IDT electrode 11 is connected with the first extraction electrode 19. The first extraction electrode 19 extends from the first IDT electrode 11 to a side opposite to the detecting portion 13, and an end portion 19e of the first extraction electrode 19 is electrically connected with the interconnection 7 formed in the first cover member 1. The second IDT electrode 12 is connected with the second extraction electrode 20. The second extraction electrode 20 extends from the second IDT electrode 12 to a side opposite to the detecting portion 13, and an end portion 20e of the second extraction electrode 20 is electrically connected with the interconnection 7.

For example, the first IDT electrode 11, the second IDT electrode 12, the first extraction electrode 19, and the second extraction electrode 20 are made of aluminum, an alloy of aluminum and cooper, or the like. The electrodes may have a multi-layer structure. When the electrodes have a multi-layer structure, for example, a first layer is made of titanium or chromium, and a second layer is made of aluminum or an aluminum alloy.

The first IDT electrode 11 and the second IDT electrode 12 are covered with a passivation film (not illustrated). The passivation film contributes to anti-oxidation of the first IDT electrode 11 and the second IDT electrode 12. For example, the passivation film is formed of a silicon oxide, an aluminum oxide, a zinc oxide, a titanium oxide, a silicon nitride, or silicon. A thickness of the passivation film is about a tenth (10 nm to 30 nm) of a thickness of the first IDT electrode 11 and the second IDT electrode 12. The passivation film may be formed to cover the entire upper surface of the substrate 10 while exposing the end portion 19e of the first extraction electrode 19 and the end portion 20e of the second extraction electrode 20.

The detecting portion 13 is formed between the first IDT electrode 11 and the second IDT electrode 12. For example, the detecting portion 13 includes a metallic film and an aptamer made of a nucleic acid or peptide immobilized to a surface of the metallic film. For example, the metallic film has a dual-layer structure including chromium and gold formed on chromium. Examples of the nucleic acid include a deoxyribo nucleic acid (DNA), a ribo nucleic acid (RNA), and a peptide nucleic acid (PNA). The details of the detecting portion 13 and the aptamer will be described later, and a description thereof is omitted.

If the first IDT electrode 11, the second IDT electrode 12 and the detecting portion 13 arranged in the y direction are assumed to be one set, two sets are installed on the sensor 100. Thus, as an aptamer immobilized to one of the detecting portions 13 is made different, it is possible to perform two types of detections through one sensor. Further, an aptamer may not be immobilized to the other one of the two detecting portions 13 and used as a reference.

The first IDT electrode 11 is covered with the first bonding member 21 as illustrated in FIG. 5. The first bonding member 21 is positioned on the upper surface of the substrate 10, and its inside is hollow. In a state in which the first bonding member 21 is placed on the upper surface of the substrate 10, the hollow portion of the first bonding member 21 serves as a first oscillation space 23. The first IDT electrode 11 is hermetically-sealed in the first oscillation space 23. Thus, the first IDT electrode 11 is isolated from external air and an analyte solution, and thus the first IDT electrode 11 can be protected. Further, as the first oscillation space 23 is protected, deteriorations of characteristics of an SAW excited in the first IDT electrode 11 can be prevented.

Figure 4A:
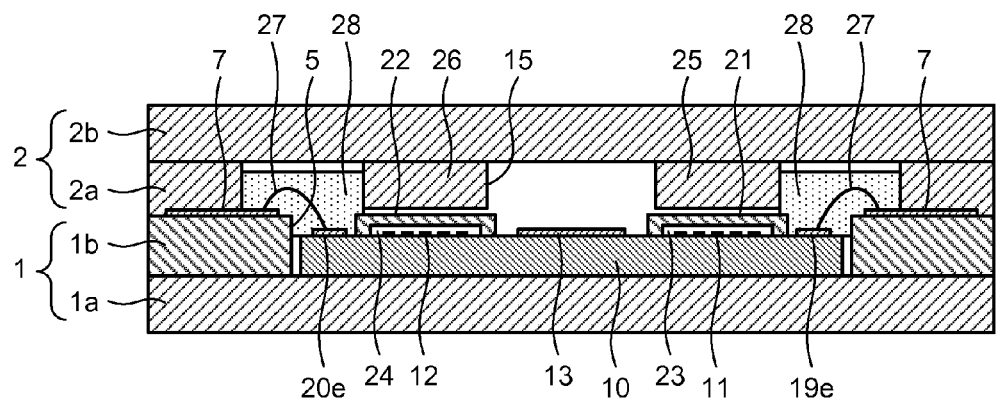
FIG. 4A is a cross-sectional view taken along line IVa-Iva' of FIG. 1.
Figure 4B:
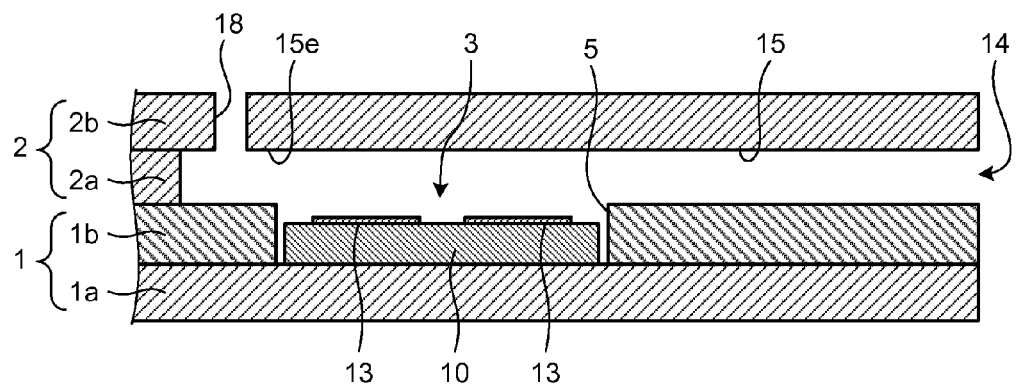
FIG. 4B is a cross-sectional view taken along line IVb-IVb' of FIG. 1.

Similarly, the second IDT electrode 12 is covered with the second bonding member 22 as illustrated in FIG. 5. The second bonding member 22 is positioned on the upper surface of the substrate 10, similarly to the first bonding member 21, and its inside is hollow as illustrated in FIG. 4A. In a state in which the second bonding member 22 is placed on the upper surface of the substrate 10, the hollow portion of the second bonding member 22 serves as a second oscillation space 24. The second IDT electrode 12 is hermetically-sealed in the second oscillation space 24. Thus, the second IDT electrode 12 is isolated from external air and an analyte solution, and thus the second IDT electrode 12 can be protected. Further, as the second oscillation space 24 is protected, deteriorations of characteristics of an SAW received in the second IDT electrode 12 can be prevented.

The oscillation space may have a rectangular parallelepiped shape, a dome shape when viewed in a cross-sectional view, or an elliptical shape when viewed in a planar view, and may have an arbitrary shape according to a shape or an arrangement of an IDT electrode or the like.

The first bonding member 21 includes a circular frame body fixed to the upper surface of the substrate 10 to surround the two first IDT electrodes 11 arranged in the x direction and a cover body fixed to the frame body to block an aperture of the frame body. For example, this structure can be formed by forming a resin film using a photosensitive resin material and patterning the resin film by a photolithography technique or the like. The second bonding member 22 can be similarly formed.

In the sensor 100, the two first IDT electrodes 11 is covered with one first bonding member 21, but the two first IDT electrodes 11 may be covered with separate first bonding members 21. Further, the two first IDT electrodes 11 may be covered with one first bonding member 21, and a partition may be formed between the two first IDT electrodes 11. For the second IDT electrode 12, similarly, the two second IDT electrodes 12 may be covered with separate second bonding members 22, and a partition may be formed between the two second IDT electrodes 12 using one second bonding member 22.

A mechanism of detecting a target substance using the detecting element 3 using an SAW in the sensor 100 will be described.

In order to detect an analyte solution in the detecting element 3 using an SAW, a certain voltage is first applied from an external measuring device to the first IDT electrode 11 through the interconnection 7, the first extraction electrode 19, and the like. In this case, in a region in which the first IDT electrode 11 is formed, the surface of the substrate 10 is excited, and an SAW having a certain frequency is generated. A part of the generated SAW is propagated toward the detecting portion 13, passes through the detecting portion 13, and then arrives at the second IDT electrode 12. Here, in the detecting portion 13, as will be described in detail later, when the analyte solution includes the first substance, a change caused by a substance having a molecular weight larger than that of the first substance occurs on the substrate surface. As a result, characteristics such as a phase of the SAW passing below the detecting portion 13 change. When the SAW whose characteristics have changed as described above arrives at the second IDT electrode 12, voltage is consequently generated at the second IDT electrode 12. The voltage is output to the outside through the second extraction electrode 20, the interconnection 7, and the like, and the external measuring device can read the voltage and inspect properties or components of the analyte solution.

In order to guide the analyte solution to the detecting portion 13, the sensor 100 uses a capillary phenomenon. Specifically, since a portion of the groove portion 15 formed below the second cover member 2 becomes a long thin tube as the second cover member 2 is bonded to the first cover member 1, it is possible to induce a capillary phenomenon to occur in the long thin tube formed by the groove portion 15 by setting the width or the diameter of the groove portion 15 to a certain value in view of a type of the analyte solution, materials of the first cover member 1 and the second cover member 2, and the like. The width (a dimension in the y direction) of the groove portion 15 is, for example, 0.5 mm to 3 mm, and the depth (a dimension in the z direction) is, for example, 0.1 mm to 0.5 mm. Further, the groove portion 15 includes an extension portion 15e serving as a portion extending beyond the detecting portion 13, and the third through hole 18 connected to the extension portion 15e is formed in the second cover member 2. As the analyte solution enters the flow channel 15, air present in the flow channel 15 is discharged to the outside through the third through hole 18.

As the tube causing the capillary phenomenon is formed in the cover member configured with the first cover member 1 and the second cover member 2, if the analyte solution comes into contact with the inlet 14, the analyte solution is absorbed into the inside of the cover member using the groove portion 15 as the flow channel. Thus, according to the sensor 100, since the sensor 100 has a mechanism of absorbing the analyte solution, it is possible to absorb the analyte solution without using a tool such as a pipette. Further, since the portion in which the inlet 14 is formed is rounded, and the inlet 14 is formed at the apex thereof, the inlet 14 is easily discerned.

Meanwhile, the flow channel 15 of the analyte solution formed by the groove portion 15 has a depth of about 0.3 mm, the detecting element 3 has a thickness of about 0.3 mm, and thus the depth of the flow channel 15 is nearly equal to the thickness of the detecting element 3. For this reason, when the detecting element 3 is placed on the flow channel 15 without change, the flow channel 15 is blocked. In this regard, in the sensor 100, as illustrated in FIG. 4, the concave portion 5 is formed in the first cover member 1 in which the detecting element 3 is mounted, and the detecting element 3 is accommodated in the concave portion 5, and thus the flow channel 15 of the analyte solution is not blocked. In other words, the flow channel 15 formed by the groove portion 15 can be secured by setting the depth of the concave portion 5 to be nearly equal to the thickness of the detecting element 3 and mounting the detecting element 3 in the concave portion 5.

Figure 3:
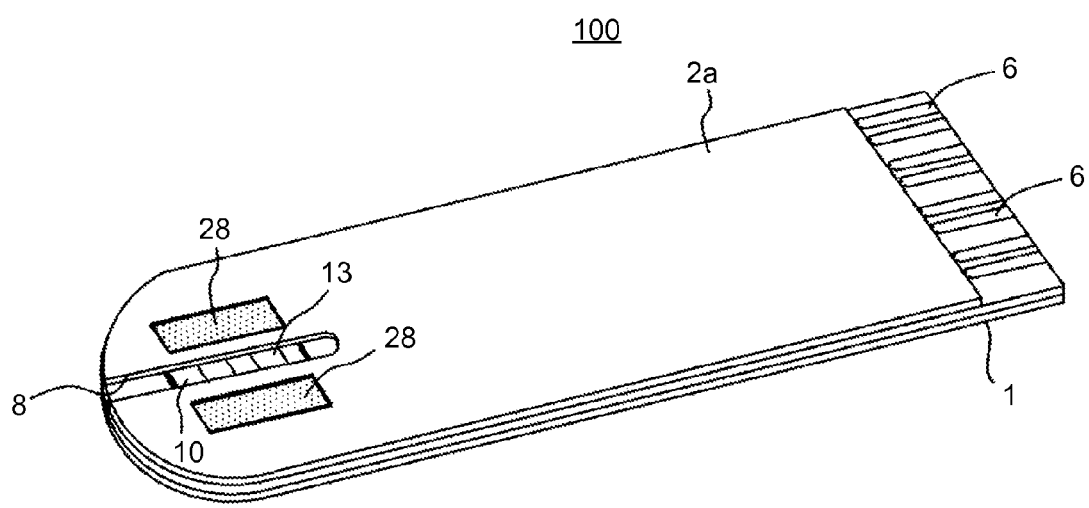
FIG. 3 is a perspective view illustrating a state in which a fourth substrate of the sensor illustrated in FIG. 1 is taken off.

FIG. 3 is a perspective view in a state in which the fourth substrate 2b of the second cover member 2 is taken off, but since the flow channel 15 of the analyte solution is secured, the analyte solution that has flown into the flow channel 15 can be smoothly guided to the detecting portion 13 by the capillary phenomenon.

From a point of view of sufficiently securing the flow channel 15 of the analyte solution, as illustrated in FIG. 4, it is preferable that the height of the upper surface of the substrate 10 from the bottom surface of the concave portion 5 is set to be equal to or smaller than the depth of the concave portion 5. For example, if the height of the upper surface of the substrate 10 from the bottom surface of the concave portion 5 is set to be equal to the depth of the concave portion 5, the bottom surface of the flow channel 15 and the detecting portion 13 can have almost the same height when the inside of the groove portion 15 is viewed from the inlet 14. In the sensor 100, the thickness of the substrate 10 is set to be smaller than the depth of the concave portion 5, and the height of the first bonding member 21 and the second bonding member 22 from the bottom surface of the concave portion 5 is set to be almost equal to the depth of the concave portion 5. If the height of the first bonding member 21 and the second bonding member 22 from the bottom surface of the concave portion 5 is set to be larger than the depth of the concave portion 5, it is necessary to process the first partition portion 25 and the second partition portion 26 of the third substrate 2a to be thinner than other portions, but as the height of the first bonding member 21 and the second bonding member 22 from the bottom surface of the concave portion 5 is set to be almost equal to the depth of the concave portion 5, the process is unnecessary, and production efficiency is good.

The plane shape of the concave portion 5 is similar to, for example, the plane shape of the substrate 10, and the concave portion 5 is slightly larger than the substrate 10. More specifically, the concave portion 5 has the size in which a gap of about 100 μm is formed between the side of the substrate 10 and the inner wall of the concave portion 5 when the substrate 10 is mounted in the concave portion 5.

For example, the detecting element 3 is fixed to the bottom surface of the concave portion 5 by a die bond material having epoxy resin, polyimide resin, silicon resin, or the like as a main component. The end portion 19e of the first extraction electrode 19 is electrically connected with the interconnection 7 by a metallic thin line 27 made of Au or the like. The same also applies in a connection between the end portion 20e of the second extraction electrode 20 and the interconnection 7. Further, the first extraction electrode 19 and the second extraction electrode 20 may be connected with the interconnection 7 by a conductive adhesive material such as Ag-paste as well as the metallic thin line 27.

Gaps are formed in connection portions between the first extraction electrode 19 and the second extraction electrode 20 and the interconnection 7. For this reason, the metallic thin line 27 is prevented from being broken when the second cover member 2 is attached to the first cover member 1. This gap can be simply formed by forming the first through hole 16 and the second through hole 17 in the third substrate 2a. Further, as the first partition portion 25 is present between the first through hole 16 and the groove portion 15, the analyte solution flowing through the groove portion 15 can be prevented from flowing into the gap formed by the first through hole 16. Thus, it is possible to prevent a short circuit from occurring by the analyte solution among a plurality of first extraction electrodes 19. Similarly, as the second partition portion 26 is present between the second through hole 17 and the groove portion 15, the analyte solution flowing through the groove portion 15 can be prevented from flowing into the gap formed by the second through hole 17. Thus, it is possible to prevent a short circuit from occurring by the analyte solution among a plurality of second extraction electrodes 20.

The first partition portion 25 is positioned on the first bonding member 21, and the second partition portion 26 is positioned on the second bonding member 22. Thus, more technically, the flow channel 15 of the analyte solution is also defined by the side wall of the first bonding member 21 at the groove portion side and the side wall of the second bonding member 22 at the groove portion side as well as the groove portion 15.

From a point of view for preventing the analyte solution from leaking to the gaps formed by the first through hole 16 and the second through hole 17, it is desirable to cause the first partition portion 25 to come into contact with the upper surface of the first bonding member 21 and cause the second partition portion 26 to come into contact the upper surface of the second bonding member 22, but in the sensor 100, a gap is present between the lower surface of the first partition portion 25 and the upper surface of the first bonding member 21, and between the lower surface of the second partition portion 26 and the upper surface of the second bonding member 22. The gaps are, for example, 10 μm to 60 μm. As the gaps are formed, for example, even when the sensor 100 is picked up by fingers and so pressure is applied to the portions, the pressure is absorbed by the gaps, and thus it is possible to prevent the pressure from being applied directly to the first bonding member 21 and the second bonding member 22. As a result, the first oscillation space 23 and the second oscillation space 24 can be prevented from being significantly deformed. Further, since the analyte solution commonly has a certain level of viscoelasticity, as the gaps of 10 μm to 60 μm are formed, the analyte solution hardly enters the gaps, and thus the analyte solution can be prevented from leaking to the gaps formed by the first through hole 16 and the second through hole 17.

The width of the first partition portion 25 is set to be larger than the width of the first oscillation space 23. In other words, the side wall of the first partition portion 25 is positioned on the frame body of the first bonding member 21. Thus, even when the first partition portion 25 comes into contact with the first bonding member 21 due to external pressure, since the first partition portion 25 is supported by the frame portion, the first bonding member 21 can be prevented from being deformed. Due to the same reason, the width of the second partition portion 26 is preferably set to be larger than the width of the second oscillation space 24.

The first extraction electrode 19, the second extraction electrode 20, the metallic thin line 27, and the interconnection 7 positioned in the gaps formed by the first through hole 16 and the second through hole 17 are covered with an insulating member 28. Thus, the electrodes and the like can be prevented from being corroded. Further, as the insulating member 28 is formed, even when the analyte solution enters the gap between the first partition portion 25 and the first bonding member 21 or the gap between the second partition portion 26 and the second bonding member 22, the analyte solution is blocked by the insulating member 28. Thus, for example, a short circuit between the extraction electrode caused by leakage of the analyte solution can be prevented.

Thus, according to the sensor 100, as the detecting element 3 is accommodated in the concave portion 5 of the first cover member 1, the flow channel 15 of the analyte solution from the inlet 14 to the detecting portion 13 can be secured, and the analyte solution absorbed from the inlet by the capillary phenomenon or the like can flow up to the detecting portion 13. In other words, it is possible to provide the sensor 100 having the absorption mechanism therein while using the detecting element 3 having the thickness. Further, for example, the flow channel 15 may include a groove portion formed on the surface of at least one of the first cover member 1 and the second cover member 2. In other words, the flow channel 15 may be formed by forming the groove portion on the surface of at least one of the first cover member 1 and the second cover member 2.

Modified Example

The above-described structure of the sensor 100 is an example, and the present invention is not limited to this example, and an arbitrary sensor 100 may be used.

Figure 7:
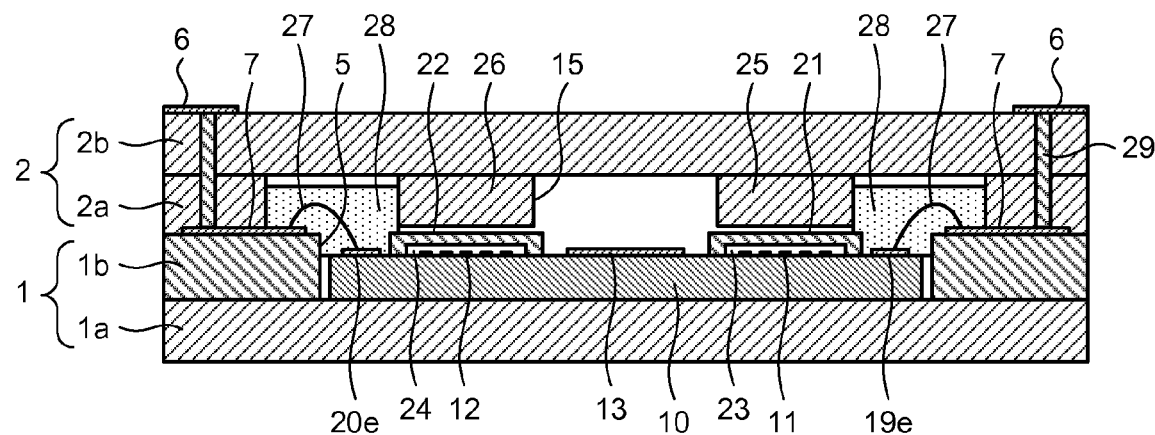
FIG. 7 is a cross-sectional view illustrating a modified example of a sensor according to an embodiment of the present invention.

For example, FIG. 7 is a cross-sectional view illustrating a modified example of the sensor 100. The cross-sectional view corresponds to the cross section illustrated in FIG. 4A. In the modified example, a position at which the terminal 6 is formed differs. In the above embodiment, the terminal 6 is formed at the other end portion of the second substrate 1b in the longitudinal direction, whereas in the modified example, the terminal 6 is formed on the upper surface of the fourth substrate 2b. The terminal 6 is electrically connected with the interconnection 7 through a through conductor 29 penetrating through the second cover member 2. The through conductor 29 is made of, for example, Ag-paste, plating, or the like. The terminal 6 may be formed on the bottom side of the first cover member 1. Thus, the terminal 6 can be formed at an arbitrary position on the surfaces of the first cover member 1 and the second cover member 2, and it is possible to decide the position according to a measuring device to be used.

Figure 8:
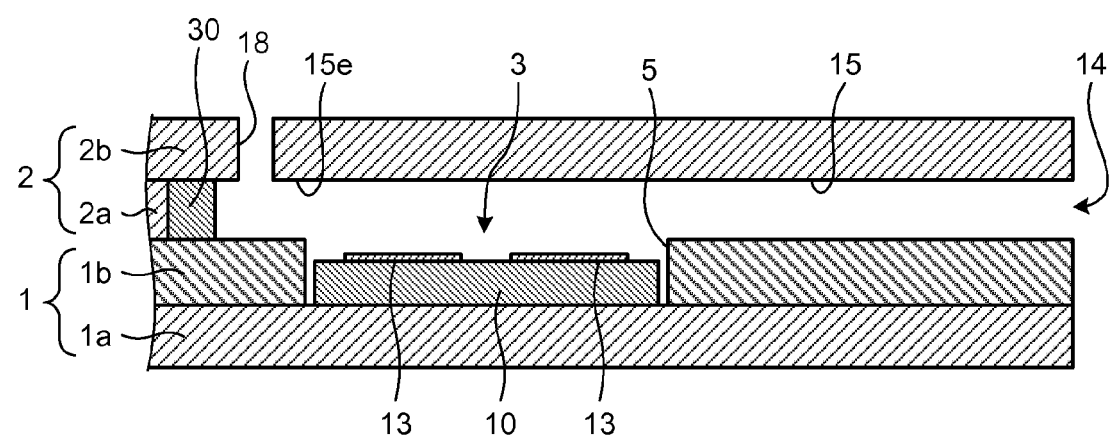
FIG. 8 is a cross-sectional view illustrating another modified example of a sensor according to an embodiment of the present invention.

Further, for example, FIG. 8 is a cross-sectional view illustrating another modified example of the sensor 100. The cross-sectional view corresponds to the cross section illustrated in FIG. 4B. In this modified example, an absorbing material 30 that absorbs the analyte solution at a predetermined speed is disposed at the end of the flow channel 15 formed by the groove portion 15. As the absorbing material 30 is disposed, an excess analyte solution is absorbed, and thus measurement can be performed in a state in which the amount of the analyte solution flowing above the detecting portion 13 is constant and stable. For example, the absorbing material 30 is made of a porous material that can absorb a liquid such as sponge.

The above embodiment has been described in connection with the example in which the detecting portion 13 includes the metallic film and the aptamer immobilized to the surface of the metallic film, but, for example, when a substance to be detected by the detecting portion 13 reacts with the metallic film, the detecting portion 13 may be configured only with the metallic film without using the aptamer. Further, a region between the first IDT electrode 11 and the second IDT electrode 12 in the surface of the substrate 10 made of a piezoelectric substrate may be used as the detecting portion 13 without using the metallic film. In this case, the surface of the substrate 10 comes into direct contact with the analyte solution to detect physical properties of the analyte solution such as viscosity. More specifically, for example, as the viscosity of the analyte solution on the detecting portion 13 changes, a change in a phase of an SAW is read.

Further, for example, the above embodiment has been described in connection with the example of the detecting element 3 including an SAW element, but, for example, the detecting element 3 in which a light waveguide or the like is formed to cause an SPR may be used. In this case, for example, a change in a refractive index of light is read in the detecting portion. As another example, the detecting element 3 in which an oscillator is formed in a piezoelectric substrate made of crystal or the like may be used. In this case, for example, a change in an oscillation frequency of the oscillator is read.

Further, for example, a plurality of types of devices may be mixedly mounted on a single substrate 10 as the detecting element 3. For example, an enzyme electrode of an enzyme electrode technique may be disposed near an SAW element. In this case, it is possible to perform measurement of an enzymatic technique in addition to an immunization technique using an antibody or an aptamer, and it is possible to increase the number of items that can be inspected at once.

Further, for example, the above embodiment has been described in connection with the example in which the first cover member 1 is configured with the first substrate 1a and the second substrate 1b, and the second cover member 2 is configured with the third substrate 2a and the fourth substrate 2b, but the present invention is not limited to this example, and a cover member in which substrates are integrated, for example, the first cover member 1 in which the first substrate 1a is integrated with the second substrate 1b may be used.

Further, for example, the above embodiment has been described in connection with the example in which one detecting element 3 is installed, but a plurality of detecting elements 3 may be installed. In this case, the concave portion 5 may be formed for each detecting element 3, and the long concave portion 5 capable of accommodating all the detecting elements 3 may be formed.

Further, for example, the groove portion 15 may be formed in either or both of the first cover member 1 and the second cover member 2. In other words, the flow channel 15 may be formed by forming grooves in both the first cover member 1 and the second cover member 2, and the flow channel 15 may be formed by forming a groove in either of the first cover member 1 and the second cover member 2.

Figure 9:
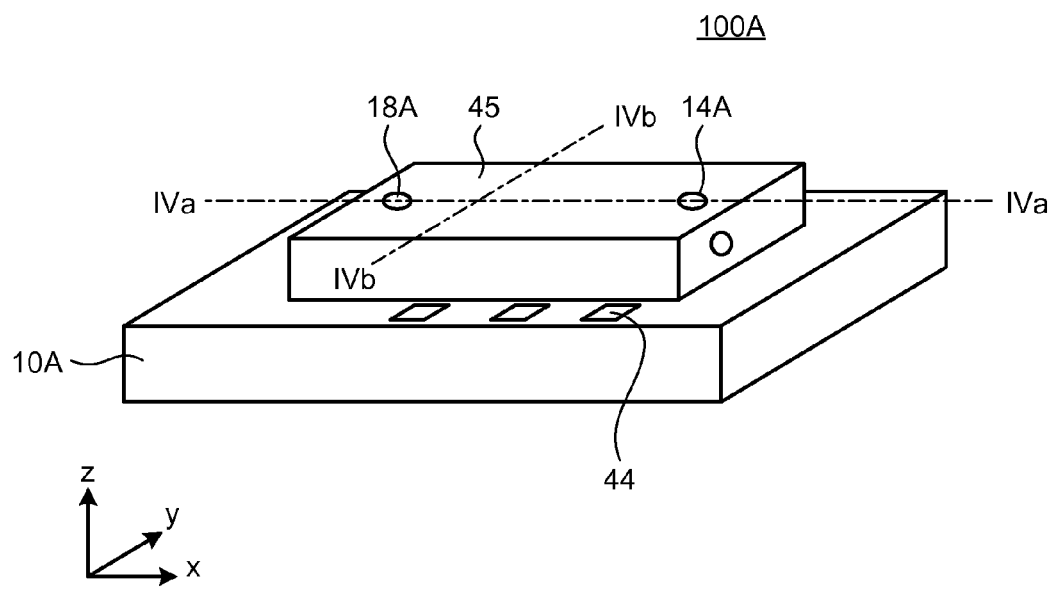
FIG. 9 is a perspective view illustrating an exemplary sensor when a cover member is bonded to a substrate.
Figure 10:
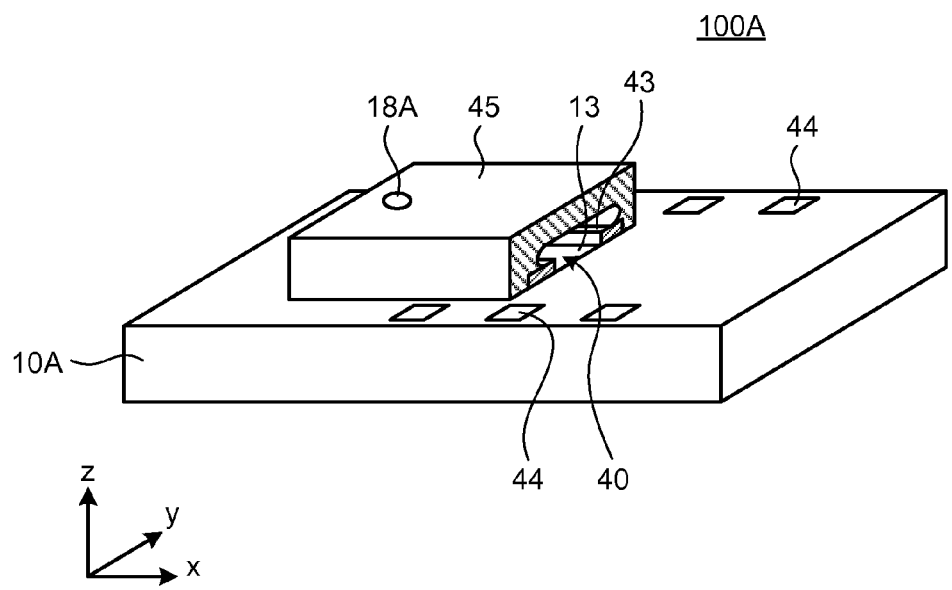
FIG. 10 is a perspective view illustrating an exemplary sensor when either half of a cover member is removed.

Further, for example, FIGS. 9 to 11 are diagrams illustrating a configuration in which a cover member 45 is bonded directly to the substrate 10. The above embodiment has been described in connection with the example in which the substrate 10 is disposed on the first cover member 1, and the first cover member 1 is bonded with the second cover member 2, but the present invention is not limited to this example. For example, the flow channel 15 may be formed such that the cover member is bonded directly to the substrate 10. The details will be described below.

FIGS. 9 to 11 will be described in connection with an example in which the flow channel 15 is formed by forming a groove in the cover member 45 bonded to a substrate 10A. The present invention is not limited to this configuration, and, for example, the flow channel 15 may be formed by forming grooves in both of the cover member 45 disposed on the upper surface of the substrate 10A and the substrate 10A, and the flow channel 15 may be formed by forming a groove in the substrate 10A.

FIG. 9 is a perspective view illustrating an exemplary sensor when a cover member is bonded to the substrate. In the example illustrated in the example illustrated in FIG. 9, the sensor 100A includes a substrate 10A and a cover member 45. The cover member 45 includes an inlet 14A serving as an inlet of the analyte solution and a third through hole 18A serving as an air hole or an outlet of the analyte solution. Further, in the example illustrated in FIG. 9, the inlet 14A is formed in the upper surface of the cover member 45, but the present invention is not limited to this example. For example, the inlet 14A may be formed in the side of the cover member 45, similarly to the sensor 100. Furthermore, in the example illustrated in FIG. 9, the cover member 45 includes pads 44. The pads 44 correspond to the end portion 19e of the first extraction electrode 19 and the end portion 20e of the second extraction electrode 20 of the sensor 100.

FIG. 10 is a perspective view illustrating an exemplary sensor when either half of a cover member is removed. FIG. 10 is a perspective view of the sensor 100A when either half of the cover member 45 is removed. As illustrated in FIG. 10, a space 40 serving as an analyte flow channel of the analyte solution is formed in the cover member 45. The inlet 14A is connected with the space 40. In other words, the analyte solution input from the inlet 14A flows into the space 40. The space 40 in the sensor 100A corresponds to the flow channel 15 in the sensor 100.

Figure 11A:
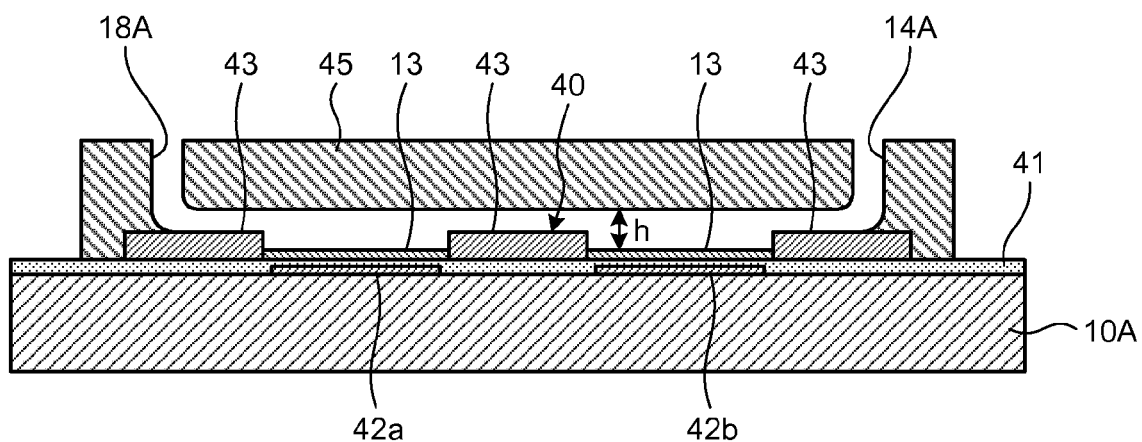
FIG. 11A is a cross-sectional view illustrating an exemplary sensor when a cover member is bonded to a substrate.
Figure 11B:
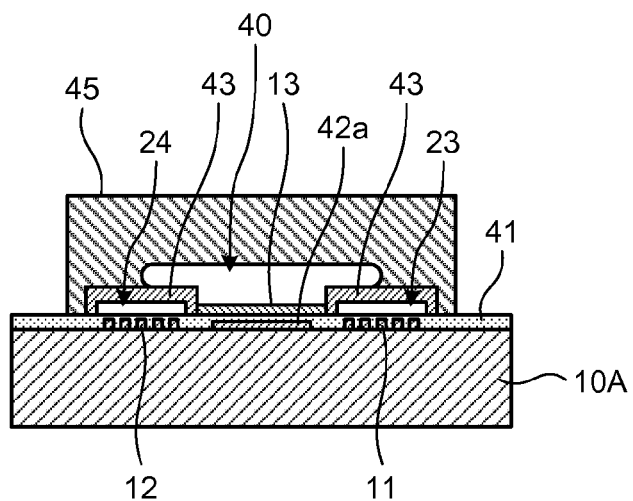
FIG. 11B is a cross-sectional view illustrating an exemplary sensor when a cover member is bonded to a substrate.

FIGS. 11A and 11B are cross-sectional views illustrating an exemplary sensor when a cover member is bonded to a substrate. FIG. 11A is a cross-sectional view taken along line IVa-IVa of FIG. 9, and FIG. 11B is a cross-sectional view taken along line IVb-IVb of FIG. 9.

As illustrated in FIGS. 11A and 11B, a first IDT electrode 11, a second IDT electrode 12, a short circuit electrode 42a, a short circuit electrode 42b, and the like are formed on the upper surface of the substrate 10A. Further, the first IDT electrode 11, the second IDT electrode 12, the short circuit electrode 42a, the short circuit electrode 42b, and the like are covered with a passivation film 41. The passivation film 41 contributes to anti-oxidation of the electrodes and the interconnections. The passivation film 41 is made of, for example, a silicon oxide, an aluminum oxide, a zinc oxide, a titanium oxide, a silicon nitride, or silicon. For example, the passivation film 41 is made of a silicon dioxide (SiO2).

The passivation film 41 is formed to cover the entire upper surface of the substrate 10A while exposing the pads 44. As the first IDT electrode 11 and the second IDT electrode 12 are covered with the passivation film 41, corrosion of the IDT electrodes can be prevented.

A thickness of the passivation film 41 is, for example, 100 nm to 10 µm. The passivation film 41 need not necessarily be formed to cover the entire upper surface of the substrate 10A, and for example, the passivation film 41 may be formed to cover only a portion around the center of the upper surface of the substrate 10A while exposing a region along an outer periphery of the upper surface of the substrate 10A including the pads 44. Further, FIGS. 11A and 11B illustrate the example in which the passivation film 41 is used, but the present invention is not limited to this example, and the passivation film 41 may not be used.

The short circuit electrode 42a and the short circuit electrode 42b serve to cause a portion of the upper surface of the substrate 10A serving as an SAW propagation channel to be electrically short circuited. As the short circuit electrode 42a and the short circuit electrode 42b are disposed, SAW loss can be reduced according to a type of SAW. Further, particularly, when a leaky wave is used as an SAW, a loss suppression effect by the short circuit electrode 42a and the short circuit electrode 42b is considered to be increased.

For example, the short circuit electrode 42a or the short circuit electrode 42b has a rectangular shape extending along the SAW propagation channel from the first IDT electrode 11 to the second IDT electrode 12. For example, the width of the short circuit electrode 42a or the short circuit electrode 42b in a direction (the x direction) orthogonal to an SAW propagation direction is equal to a cross width of the electrode fingers of the first IDT electrode 11. Further, the end portion of the short circuit electrode 42a or the short circuit electrode 42b at the first IDT electrode side in a direction (the y direction) parallel to the SAW propagation direction is positioned at a distance of a half wavelength of an SAW from the center of the electrode fingers positioned at the end portion of the first IDT electrode 11. Similarly, the end portion of the short circuit electrode 42a or the short circuit electrode 42b at the second IDT electrode 12 in the y direction is positioned at a distance of a half wavelength of an SAW from the center of the electrode fingers positioned at the end portion of the second IDT electrode 12.

Here, frequency characteristics can be designed using the number of electrode fingers of the first IDT electrode 11 and the second IDT electrode 12, a distance between neighboring electrode fingers, a cross width of the electrode finger, and the like as parameters. Examples of the SAW excited by the IDT electrode include a Rayleigh wave, a love wave, and a leaky wave. Further, an elastic member for anti-reflection of an SAW may be disposed in a region outside the first IDT electrode 11 in the SAW propagation direction. For example, the frequency of an SAW can be set within a range from several megahertz (MHz) to several gigahertz (GHz). Here, when a frequency of an SAW is set to hundreds of MHz to 2 GHz, it is practical, and downsizing of the substrate 10A and downsizing of the sensor 100A can be implemented.

The short circuit electrode 42a or the short circuit electrode 42b may be in an electrically floating state, or a pad 44 for ground potential may be disposed, and the short circuit electrode 42a or the short circuit electrode 42b may be connected to the pad 44 and have ground potential. When the short circuit electrode 42a or the short circuit electrode 42b has ground potential, propagation of a direct wave by electromagnetic coupling between the first IDT electrode 11 and the second IDT electrode 12 can be suppressed.

For example, the short circuit electrode 42a or the short circuit electrode 42b may be made of aluminum, an alloy of aluminum and copper, or the like. The electrodes may have a multi-layer structure. When the electrodes have a multi-layer structure, for example, a first layer is made of titanium or chromium, and a second layer is made of aluminum or an aluminum alloy.

Plate-like bodies 43 have concave portions for forming the first oscillation space 23 and the second oscillation space 24, and as the plate-like bodies 43 are bonded to the substrate 10A, the first oscillation space 23 and the second oscillation space 24 are formed. For example, the plate-like bodies 43 are formed using a photosensitive resist. The plate-like bodies 43 correspond to the first bonding member 21 and the second bonding member 22 in the sensor 100. In the example illustrated in FIGS. 11A and 11B, a penetrating portion penetrating through the plate-like bodies 43 in the depthwise direction is formed between the concave portions of the plate-like bodies 43 for forming the first oscillation space 23 and the second oscillation space 24. The penetrating portion is formed to form a metallic film on an SAW propagation channel. In other words, when the plate-like body 43 is bonded to the substrate 10A, if viewed in a planar view, at least a part of the propagation channel of an SAW propagating from the first IDT electrode 11 to the second IDT electrode 12 is exposed from the penetrating portion, and the detecting portion 13 is formed in the exposed portion.

Further, for example, an arbitrary process may be performed on the detecting portion 13. For example, when one of the two detecting portions 13 is used as a reference, a process of preventing a substance detected by the detecting portion 13 from being attached to the metallic film used as the reference may be performed. A concrete example in which the detecting portion 13 is combined with a nucleic acid such as DNA will be described. In this case, since a nucleic acid such as DNA is negatively changed, by negatively charging the metallic film of the detecting portion 13 used as a reference through an arbitrary technique, it is possible to prevent a nucleic acid such as DNA from being erroneously attached to the reference. Similarly, since a nucleic acid such as DNA tends to be attached to gold, a metallic film made of metal other than gold may be used as the metallic film of the detecting portion 13 used as the reference. Further, for example, when a signal substance is a nucleic acid, a nucleic acid of a random arrangement may be immobilized to the reference to be same as at the detection side. As a result, as the surface state of the reference becomes the same as the surface state of the detection side, it is possible to cancel, for example, a small difference in viscosity considered to be caused by a difference between surfaces, and it is possible to regard only combination at the detection side as a difference between the reference and the detection side.

The sensor according to the above embodiment and the sensors according to various kinds of modified examples are effective in detecting a small molecule, and can be used for the general purpose for maintaining beauty or youth such as a fatigue or anti-aging marker as well as for the purpose for use in an existing medical system such as a cancer marker. Here, an SAW chip serving as a high-sensitivity transducer is embedded as a disposable sensor, and a signal substance (or an aptamer itself) dissociated from an aptamer is combined with/disassociated from a substrate surface in a capillary flow channel on the SAW chip, and thus it is possible to implement a sensor that is high in sensitivity to a small molecule, disposable, light in weight, compact, and small in size. As a result, it is possible to implement a small simple sensor.

For example, a variable structure type aptamer mass change detecting portion is disposed on an SAW propagation channel, and thus propagation of an SAW interacts with a signal substance or an aptamer. As a result, for example, it is possible to directly detect a mass change in which an amount of a target detection object is increased, it is easy to perform conversion for quantification, and it is possible to amplify a signal and perform detection with a high degree of accuracy. Further, a signal substance or an aptamer is larger in mass than a small molecule to be detected, and a detection result can be amplified.

Further, for example, a SAW propagation channel serving as a portion reacting with a biological substance and an IDT electrode serving as a portion performing conversion into an electric signal can be finely manufactured on a single substrate. As a result, a very small sensor can be implemented, mass production is possible in a wafer process or the like, and a disposable sensor chip can be simply implemented.

Further, for example, an SAW detecting circuit has a circuit configuration similar to that employed in communication devices such as many wireless terminals or tablet terminals, and thus the detecting circuit of the sensor can be simply connected to an electronic device such as a wireless terminal or a tablet terminal.

Detecting Portion of Sensor According to First Embodiment

In an embodiment, the sensor 100 according to the disclosure includes the substrate 10. In an embodiment, the sensor 100 according to the disclosure further includes a combining portion 240, and the combining portion 240 is positioned on the surface of the substrate 10, can be combined with a second substance 220 having a molecular weight larger than a molecular weight of the first substance 210, and can detect whether or not the first substance 210 is included in an analyte including the second substance 220 and an aptamer 230 that can be combined with the first substance 210 and the second substance 220. The second substance 220 is also referred to as a "signal substance."

For example, the sensor 100 includes the combining portion 240 that is combined with the second substance 220 having a molecular weight larger than that of the first substance 210. Further, for example, in the sensor 100, the combining portion 240 detecting whether or not the first substance 210 is included in the analyte that has come into contact with both the aptamer 230 that includes a first combining part 231 for the first substance 210 and a second combining part 232 for the second substance 220 and is combined with either of the first substance 210 and the second substance 220 and the second substance 220 is disposed on the surface of the substrate 10.

Here, the first substance 210 is an arbitrary substance. For example, the first substance 210 is a low molecular (small molecular) organic compound such as protein, an enzyme, a cell, a cell tissue, microorganism, a virus, a bacterium, toxin, nucleic acid, a saccharide, a lipid, metabolite, or an adenosine TriPhosphate (ATP). Further, for example, the first substance 210 is an arbitrary substance serving as a marker indicating a body condition such as stress, fatigue, and various kinds of diseases, induced pluripotent stem cell (iPS), or the like.

The second substance 220 is an arbitrary substance having a molecular weight larger than that of the first substance 210. For example, the second substance 220 is an enzyme, protein, a nucleic acid, or the like. More preferably, the second substance 220 is a nucleic acid. Using a nucleic acid, it is possible to simply control bond strength between the second combining part 232 and the second substance 220 by changing a base number forming a complementary strand.

Here, the molecular weight of the first substance 210 and the molecular weight of the second substance 220 are supplementarily described. The second substance 220 is preferably a substance having a molecular weight larger than the first substance 210. For example, the molecular weight of the second substance 220 is 10,000 or more. For example, the molecular weight of the first substance 210 is 500 or less, and more preferably 200 to 500. Here, the present invention is not limited to this example, the molecular weights of the first substance 210 and the second substance 220 may have an arbitrary value.

The aptamer refers to a substance that is high in affinity for a specific substance and specifically combined with a specific substance. The following description will proceed with an example of using a nucleic acid aptamer serving as the aptamer 230 formed of a nucleic acid, but the present invention is not limited to this example, a peptide aptamer may be used, and an arbitrary aptamer 230 may be used. Further, when a nucleic acid aptamer is used, various kinds of modifications may be performed on a nucleic acid forming a nucleic acid aptamer. Further, an exemplary base sequence of the aptamer 230 in which the first substance 210 is ATP is indicated by a sequence number 1.

FIG. 12 is a diagram for describing an exemplary aptamer according to an embodiment of the disclosure. In the example illustrated in FIG. 12, for convenience of description, in addition to the aptamer 230, the first substance 210 and the second substance 220 are illustrated. Further, for convenience of description, FIG. 12 will be described in connection with an example in which the aptamer 230 combined with the second substance 220 is mixed with the analyte solution, and the aptamer 230 and the second substance 220 come into contact with the analyte solution. Here, the present invention is not limited to this example, and by causing the aptamer 230 and the second substance 220 to be attached to the flow channel 15 of the sensor in advance, the analyte solution coming into contact with the aptamer 230 and the second substance 220 may come into contact with the detecting portion 13. At this time, the aptamer 230 combined with the second substance 220 in advance may be combined with the side of the flow channel 15 so that the aptamer 230 is not separated from the side of the flow channel 15. Further, by causing the aptamer 230 and the second substance 220 to be attached to or combined with the side of the flow channel 15 of the sensor at the inlet side rather than the detecting portion 13, the aptamer 230 and the second substance 220 may be caused to come into contact with the analyte solution with a high degree of accuracy before arriving at the detecting portion 13.

In other words, for example, since the aptamer 230 and the second substance 220 are attached to the groove portion 15, the combining portion 240 may detect the first substance 210 from the analyte that has come into contact with the aptamer 230 and the second substance 220 being attached to the groove portion 15. Further, for example, since the aptamer 230 is immobilized to the groove portion 15 and combined with the second substance 220, the combining portion 240 may detect the first substance 210 from the analyte that has come into contact with the aptamer 230. Here, for example, the aptamer 230 being combined with the second substance 220 is chemically combined with a surface substance of the groove portion 15.

Here, at least one of the aptamer 230 and the analyte may be positioned, away from the combining portion 240. Further, at least one of the aptamer 230 and the analyte may be positioned in the groove portion 15. Furthermore, at least one of the aptamer 230 and the analyte may be positioned in the detecting portion.

Further, when the aptamer 230 and the second substance 220 are attached to the flow channel 15 in advance, it is important to employ a dry form and cause the aptamer 230 and the second substance 220 to be attached to the flow channel 15 in a separable form so that at least the second substance 220 is separated from the flow channel 15 by contact with the analyte solution and comes into contact with the detecting portion 13 together with the analyte solution.

(1) of FIG. 12 illustrates an example in which the first substance 210 is not included in the analyte solution, and (2) of FIG. 12 illustrates an example in which the first substance 210 is included in the analyte solution.

As illustrated in FIG. 12, the aptamer 230 according to the disclosure includes the first combining part 231 for the first substance 210 and the second combining part 232 for the second substance 220, and is combined with either of the first substance 210 and the second substance 220.

As illustrated in FIG. 12, the aptamer 230 includes the first combining part 231 that is combined with the first substance 210 and the second combining part 232 that is combined with the second substance 220. As illustrated in (1) of FIG. 12, the aptamer 230 is designed such that the second combining part 232 is combined with the second substance 220 when the first substance 210 is not present in the analyte solution. On the other hand, as illustrated in (2) of FIG. 12, the aptamer 230 is designed such that the first combining part 231 is combined with the first substance 210, and the second substance 220 combined with the second combining part 232 is disassociated from the aptamer 230 when the first substance 210 is present in the analyte solution. In other words, when the first substance 210 is not present in the analyte solution, the aptamer 230 and the second substance 220 form a complex. Meanwhile, when the first substance 210 is present in the analyte solution, the aptamer 230 is disassociated from the second substance 220, and the aptamer 230 is combined with the first substance 210 to form a complex. In other words, the aptamer 230 is designed to be combined with the first substance 210 in preference to the second substance 220.

Here, a mechanism in which when the first substance 210 is present in the analyte solution, the first combining part 231 is combined with the first substance 210, and the second substance 220 combined with the second combining part 232 is disassociated from the aptamer 230 is supplementarily described. For example, the second substance 220 being combined with the second combining part 232 is disassociated from the first combining part 231 due to influence on a steric structure of the aptamer 230 caused by a combination of the first substance 210 and the first combining part 231, influence of a steric barrier by the first substance 210 combined with the first combining part 231, or the like. Here, a mechanism in which the second substance 220 is disassociated from the aptamer 230 is not limited to this example, and an arbitrary mechanism may be used.

Here, a design technique of designing the aptamer 230 having the mechanism in which when the first substance 210 is present in the analyte solution, the first combining part 231 is combined with the first substance 210, and the second substance 220 combined with the second combining part 232 is disassociated from the aptamer 230 is supplementarily described. The following description will proceed with an example of using single-strand DNA having a molecular weight of about 15,000 as the second substance 220 for convenience of description, but the present invention is not limited to this example, and RNA, PNA, or an arbitrary substance may be used as the second substance 220. An exemplary technique of deciding the base sequence the first combining part 231, an exemplary technique of deciding the base sequence of the second combining part 232, and an exemplary technique of deciding the base sequence of the aptamer 230 will be described below in the described order.

An exemplary technique of deciding the base sequence of the first combining part 231 is now described. For example, the base sequence of the first combining part 231 may be decided by an in vitro selection technique, a systematic evolution of ligands by exponential enrichment (SELEX) technique, or the like. In further detail, the base sequence of the first combining part 231 or the second combining part 232 is decided such that the aptamer 230 that is specifically combined with the first substance 210 is acquired by the in vitro selection technique or the SELEX technique, and the base sequence of the acquired aptamer 230 is decoded. Here, the present invention is not limited to this example. For example, when the first substance 210 is a nucleic acid, a base sequence complementary to a part or whole of the nucleic acid serving as the first substance 210 may be used instead of the in vitro selection technique, the SELEX technique, or the like.

An exemplary technique of deciding the base sequence of the second combining part 232 is now described. The base sequence of the second combining part 232 may be decided in a manner similar to the first combining part 231. Further, when a nucleic acid is used as the second substance 220, a base sequence complementary to a part or whole of a nucleic acid serving as the second substance 220 may be used as the base sequence of the first combining part 231 instead of the in vitro selection technique, the SELEX technique, or the like. Here, as the second substance 220, a substance having a molecular weight larger than that of the first substance 210 is used, and more preferably, a substance having a molecular weight of 10,000 or more is used. Thus, when the base sequence complementary to the whole of the nucleic acid serving as the second substance 220 is used, combination strength is too large, and it is not disassociated, and thus it is desirable to use the base sequence complementary to a part of the nucleic acid as the second combining part 232.

An exemplary technique of deciding the base sequence of the aptamer 230 is now described. The base sequence of the aptamer 230 is decided based on the base sequence of the first combining part 231 and the base sequence of the second combining part 232. For example, the base sequence of the aptamer 230 may be decided so that the base sequence of the first combining part 231 is terminally combined with the base sequence of the second combining part 232. Here, the present invention is not limited to this example, and the base sequence in which the base sequence of the second combining part 232 is inserted into the base sequence of the first combining part 231 may be used, and the base sequence in which the base sequence of the first combining part 231 is inserted into the base sequence of the second combining part 232 may be used.

Further, the second combining part 232 may be formed by a part of the base sequence of the first combining part 231. In this case, the second substance 220 is a nucleic acid having a base sequence complementary to the second combining part 232 serving as a part of the first combining part 231. Further, the second combining part 232 may be formed by a part of a base sequence of the first combining part 231 at the 3 terminal side or the 5 terminal side and a base sequence independent of the second combining part 232.

Further, an arbitrary base sequence may be used as a base sequence other than the part of the base sequence of the second substance 220 complementary to the second combining part 232. Preferably, the base sequence other than the part complementary to the second combining part 232 may be a base sequence that does not have a sequence complementary to a part or whole of the first combining part 231 or the second combining part 232. For example, a base sequence in which one arbitrary base continues up to the terminal may be used.

Here, the base number of the second combining part 232 is supplementarily described. As the base number of the second combining part 232 increases, combination strength between the second combining part 232 and the second substance 220 increases. As a result, as the base number of the second combining part 232 increases, the second combining part 232 is more likely to be combined with the second substance 220, and when the first substance 210 is combined with the first combining part 231, the second substance 220 is unlikely to be disassociated from the second combining part 232. Similarly, as the base number of the second combining part 232 decreases, the combination strength between the second combining part 232 and the second substance 220 decreases. As a result, as the base number of the second combining part 232 decreases, the second combining part 232 is unlikely to be combined with the second substance 220, and when the first substance 210 is combined with the first combining part 231, the second substance 220 is likely to be disassociated from the second combining part 232. For this reason, the base number of the second combining part 232 has an appropriate range, and is preferably "20" or less, and more preferably "9 to 11."

The analyte solution may be an arbitrary solution including a liquid or a solid serving as a detection target, and the analyte solution comes into contact with the aptamer 230 and the second substance 220 as the aptamer 230 and the second substance 220 are added to and mixed in the analyte solution in advance, or the analyte solution passes through the flow channel 15 of the sensor 100 and comes into contact with the aptamer 230 and the second substance 220 attached or immobilized to the flow channel 15. Further, for the ratio of the aptamer 230 and the second substance 220 coming into contact with the analyte solution, preferably, the mole ratio of the aptamer 230 is equal to or larger than the mole ratio of the second substance 220, and more preferably, the mole ratio of the aptamer 230 is equal to the mole ratio of the second substance 220.

Further, the combining portion 240 for the second substance 220 for detecting whether or not the first substance 210 is included in the analyte solution is disposed on the surface of the substrate 10. The detecting portion 13 may be the entire substrate surface or a part of a substrate surface. For example, the detecting portion 13 includes the metallic film and the combining portion 240 immobilized to the metallic film. Here, the present invention is not limited to this example, and the detecting portion 13 may not include the metallic film. When the detecting portion 13 includes the metallic film, any metal may be used to form the metallic film. For example, preferably, Au (gold), Ti, Cu, or the like is used, and more preferably, gold is used.

Here, the combining portion 240 of the substrate surface is described. An arbitrary substance that is specifically combined with the second substance 220 is used as the combining portion 240 of the substrate surface. For example, an aptamer, protein, or an antibody which is specifically combined with the second substance 220 is used as the combining portion 240 of the substrate surface. For example, the combining portion 240 of the substrate surface is decided in a manner similar to the second combining part 232. Here, an arbitrary substance that is specifically combined with the second substance 220 is not limited to the example of using an aptamer, protein, or an antibody. For example, when a material forming a substrate surface is combined with the second substance 220, a separate aptamer, protein, or an antibody may not be used.

An immobilizing technique of immobilizing the combining portion 240 to the substrate surface is now described. An arbitrary technique may be used as the immobilizing technique. For example, immobilization may be performed using strong affinity between streptavidin and biotin. In this case, for example, streptavidin is immobilized to the detecting portion 13 in advance. In further detail, streptavidin is immobilized onto the surface on which a self-assembled monolayer (SAM) made of alkylthiol or the like is formed in advance to cover the surface (Au or the like) of the detecting portion 13 as much as possible when immobilized. Further, biotin is immobilized to an end portion of a substance used as the combining portion 240 of the substrate surface in advance, and a solution of a substance used as the combining portion 240 of the substrate surface is prepared. Thereafter, the solution including the substance used as the combining portion 240 of the substrate surface is caused to come into contact with the detecting portion 13, and thus the combining portion 240 is immobilized to the detecting portion 13. Thereafter, in order to remove a substance that is not immobilized to the detecting portion 13 and remains in the detecting portion 13, the detecting portion 13 may be cleaned using an arbitrary solvent. For example, NaOH is used as a solvent used for cleaning. Here, a solvent used for cleaning is not limited to NaOH, and an arbitrary solvent may be used.

Here, a relation among the first substance 210, the aptamer 230, and the combining portion 240 is supplementarily described. The first substance 210, the aptamer 230, and the combining portion 240 have a magnitude relation related to a free energy change. Specifically, there is a magnitude relation in which a first free energy change calculated from a dissociation constant of the first substance 210 and the aptamer 230 is smaller than a second free energy change associated with a combination of the aptamer 230 and the second substance 220. Further, there is a magnitude relation in which a third free energy change associated with a combination of the second substance 220 and the combining portion 240 is larger than the second free energy change.

In other words, the first free energy change calculated from the dissociation constant of the first substance 210 and the aptamer 230 is smaller than the second free energy change associated with a combination of the aptamer 230 and the second substance 220, and the third free energy change associated with a combination of the second substance 220 and the combining portion 240 is larger than the second free energy change.

The free energy indicates a free energy change of Gibbs and has a negative value. It is because when a spontaneous reaction occurs, a free energy has a negative value. As the free energy change of Gibbs increases in a negative direction, a reaction is more likely to proceed. In other words, for example, the "magnitude relation in which the first free energy change is smaller than the second free energy change" indicates a magnitude relation in which both the first free energy change and the second free energy change have a negative value, and an absolute value of the first free energy change is larger than an absolute value of the second free energy change.

Here, the description will proceed with an example in which the aptamer 230 and the combining portion 240 have a base sequence complementary to a part of the base sequence of the second substance 220. Further, the description will proceed with an example in which the combining portion 240 has a base sequence complementary to a part of the base sequence of the second substance 220. Furthermore, the description will proceed with an example in which the second free energy is a free energy change associated with a combination of the complementary parts of the base sequence of the aptamer 230 and the base sequence of the second substance 220. Moreover, the description will proceed with an example in which the third free energy is a free energy change associated with a combination of the complementary parts of the base sequence of the second substance 220 and the base sequence of the combining portion 240. In this case, the base type and the base number of the complementary base sequence between the aptamer 230 and the second substance 220 and the base type and the base number of the complementary base sequence between the combining portion 240 and the second substance 220 have values satisfying the magnitude relation among the first free energy change, the second free energy change, and the third free energy change.

In other words, the description will proceed with an example in which each of the aptamer 230 and the combining portion 240 have the base sequence. Further, the description will proceed with an example in which the base sequence of the aptamer 230 has a part complementary of a first part of the base sequence of the second substance 220, and the base sequence of the combining portion 240 has a part complementary to a second part of the base sequence of the second substance 220. Furthermore, the description will proceed with an example in which the second free energy change is a free energy change associated with a combination of the complementary parts of the first part of the base sequence of the second substance 220 and the base sequence of the aptamer 230. The description will proceed with an example in which the third free energy change is a free energy change associated with a combination of the complementary parts of the second part of the base sequence of the second substance 220 and the base sequence of the combining portion 240. In this case, the base type and the base number of the complementary base sequence between the aptamer 230 and the second substance 220 and the base type and the base number of the complementary base sequence between the combining portion 240 and the second substance 220 have values satisfying the magnitude relation among the first free energy change, the second free energy change, and the third free energy change.

Further, the aptamer 230 may be combined with or attached to the SAW propagation channel or the flow channel 15 in advance, and may be melted and included in the analyte solution before the analyte solution flows into the flow channel 15 of the sensor 100. For example, at least one of the aptamer 230 and the analyte is positioned away from the combining portion 240 or the detecting portion 13. Further, for example, at least one of the aptamer 230 and the analyte is positioned in the flow channel 15. Furthermore, for example, at least one of the aptamer 230 and the analyte is positioned in the combining portion 240 or the detecting portion 13.

Further, a change in a propagation constant of an SAW is limited to a change in a surface of a substrate. As a result, for example, a process of removing a non-reacted substance that has not reacted with a target even when the non-reacted substance remains on the substrate is not particularly necessary. Through an operation of simply causing the analyte solution to flow into the capillary flow channel, a signal substance or an aptamer associated with a combination with a target is combined with/disassociated from (a part functioning as) a receptor (such as a combining portion) immobilized to the substrate surface, and thus it is possible to selectively detect influence by combining and disassociating.

Detection Method According to First Embodiment

In an embodiment, a detection technique according to the disclosure includes a contact process of causing an analyte to come into contact with the surface of the substrate 10 of the sensor having the combining portion 240 for the second substance 220, and the analyte includes the first combining part 231 for the first substance 210 and the second combining part 232 for the second substance 220 having a molecular weight larger than that of the first substance 210, and comes into contact with both the aptamer 230 that is combined with either of the first substance 210 and the second substance 220 and the second substance 220.

Further, when the aptamer 230, the second substance 220, and the analyte are added to and mixed in the analyte solution in advance, mixing may be performed using an arbitrary technique. For example, the aptamer 230, the second substance 220, and the analyte may be mixed and prepared, the aptamer 230 in which the second substance 220 is combined with the second combining part 232 in advance and the analyte may be mixed and prepared, or an arbitrary technique may be used.

Here, when the aptamer 230, the second substance 220, and the analyte are added to and mixed in the analyte solution in advance, preferably, the aptamer 230 in which the second substance 220 is combined with the second combining part 232 in advance and the analyte solution may be mixed and prepared. Using the aptamer 230 in which the second substance 220 is combined with the second combining part 232 in advance, although the first substance 210 is not present, the second substance 220 is not combined with the aptamer 230, and thus it is possible to reduce a phenomenon that the second substance 220 is combined with the combining portion 240 and improve a detection accuracy.

An arbitrary technique may be used as a technique of combining the second substance 220 with the second combining part 232 in advance. The description will continue with an example in which the second substance 220 is a nucleic acid, and the second combining part 232 is a nucleic acid complementary to the second combining part 232. In this case, since the second substances 220 do not form a double strand, and the second combining parts 232 of the aptamer 230 do not form a double strand, the second substance 220 may be combined with the second combining part 232 in advance by mixing and stirring at a room temperature. Further, for example, by heat denaturation under a reaction condition in a polymerase chain reaction (PCR) technique, a double strand DNA is converted into a single strand with a high degree of accuracy, and a primer is annealed on a single strand DNA with a high degree of accuracy. For this reason, the second substance 220 may be combined with the second combining part 232 in advance using a temperature condition in the PCR technique. In further detail, the second substance 220 may be combined with the second combining part 232 in advance such that the second substance 220 is mixed with the aptamer 230, and then the mixture of the second substance 220 and the aptamer 230 is heated to a temperature at which a double strand DNA is converted into a single strand by heat denaturation and thereafter cooled.

Further, a technique of causing the analyte solution to come into contact with the substrate surface may be an arbitrary technique. For example, when the sensor 100 serving as the SAW sensor is used, the analyte solution may be caused to come into contact with the substrate surface by guiding the analyte solution from the inlet 14 to the detecting portion 13 via the groove portion 15 as described above. Further, when the sensor is a measuring cell of an SPR device or a QCM crystal sensor, the analyte solution may be manually caused to come into contact with a substrate surface of a biocell, or the analyte solution may be caused to come into contact with a flow cell of the SPR device or the QCM measuring device by injecting the analyte solution into the flow cell.

Figure 13:
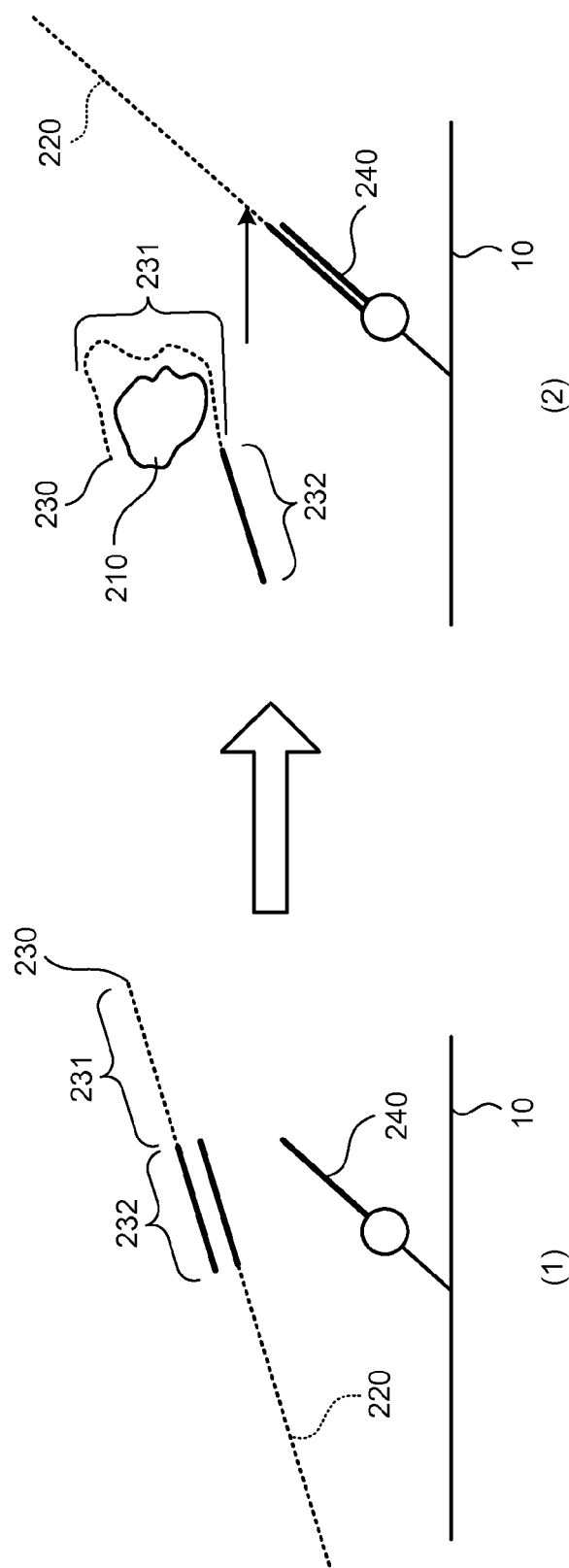
FIG. 13 is a diagram for describing a state change of a substrate surface.

Further, the detection technique according to the disclosure includes a detecting process of detecting the first substance 210 from the analyte by detecting the state change of the surface of the substrate 10 with which the analyte has come into contact. FIG. 13 is a diagram for describing a state change of a substrate surface. FIG. 13 will be described in connection with an example in which, for convenience of description, an analyte solution for detection is prepared by mixing the aptamer 230 being combined with the second substance 220 with the analyte solution. (1) of FIG. 13 illustrates an example in which the first substance 210 is not included in the analyte solution, and (2) of FIG. 13 illustrates an example in which the first substance 210 is included in the analyte solution. In FIG. 13, for example, a metallic layer serving as the detecting portion 13 positioned on the upper surface of the substrate 10 is not illustrated.

As illustrated in (1) of FIG. 13, when the first substance 210 is not present in the analyte solution, the aptamer 230 is combined with the second substance 220 through the second combining part 232, and thus the combining portion 240 immobilized to the substrate surface is not combined with the second substance 220. On the other hand, as illustrated in (2) of FIG. 13, when the first substance 210 is present in the analyte solution, the first combining part 231 is combined with the first substance 210, and the second substance 220 being combined with the first combining part 231 is disassociated from the aptamer 230. Then, the disassociated second substance 220 is combined with the combining portion 240 immobilized to the substrate surface.

Here, the state change of the substrate surface refers to a mass change, a dielectric constant change, a viscoelasticity change, a propagation characteristics change, a resonance frequency change, and the like which are caused as the combining portion 240 immobilized to the substrate surface is combined with the second substance 220. For example, when measuring is performed using the SPR device, if the combining portion 240 immobilized to the substrate surface is combined with the second substance 220, a mass or a dielectric constant of the substrate surface changes, and due to this change, an SPR angle change occurs. In this case, the state change of the substrate surface is a mass change or a dielectric constant change caused by a combination of the combining portion 240 and the second substance 220, and the state change of the substrate surface is detected by detecting the SPR angle change. Further, when the SAW sensor is used, a propagation characteristics change is caused by a mass change or a viscoelasticity change of the substrate surface. In this case, the state change of the substrate surface is a mass change or a viscoelasticity change caused by a combination of the combining portion 240 and the second substance 220, and the state change of the substrate surface is detected by detecting the propagation characteristics change. Further, when the QCM measuring device is used, a resonance frequency change is caused by a mass change of the substrate surface. In this case, the state change of the substrate surface is the mass change caused by a combination of the combining portion 240 and the second substance 220, and the state change of the substrate surface is detected by detecting the resonance frequency change.

The change of the substrate surface is caused by a combination of the combining portion 240 immobilized to the substrate surface and the second substance 220, and the combining portion 240 immobilized to the substrate surface is combined with the second substance 220 when the first substance 210 is included in the analyte solution. Further, the second substance 220 has a molecular weight larger than a molecular weight of the first substance 210. As a result, compared to the technique of detecting the change of the substrate surface caused by a combination of the first substance 210 and the substrate surface, the technique of detecting the change of the substrate surface caused by a combination of the second substance 220 and the substrate surface is larger in a mass change, a dielectric constant change, and a viscoelasticity change in the substrate surface and thus can improve the detection sensitivity. Accordingly, it is possible to detect a small molecule that is hardly measured by the technique of the related art of immobilizing a small molecule to a substrate surface and detecting a small molecule.

Detection System and Detection Device According to First Embodiment

In an embodiment, the detection system according to the disclosure includes a sensor including a combining portion 240 for a second substance 220 having a molecular weight larger than that of a first substance 210 and a substrate 10 including the combining portion 240 disposed on its surface.

Here, the sensor used in the first embodiment of the detection system and the detection device is the same as the above-described sensor, and a description thereof is omitted.

Next, in an embodiment, the detection system according to the disclosure further includes a detection device. The detection device includes a detection control unit that detects whether or not the first substance 210 is included in the analyte by detecting the state change of the surface of the substrate 10 when the analyte coming into contact with the aptamer 230 that includes the first combining part 231 for the first substance 210 and the second combining part 232 for the second substance 220 and combines with either of the first substance 210 and the second substance 220 and the second substance 220 comes into contact with the surface of the substrate 10 of the sensor including the combining portion 240 for the second substance 220 having a molecular weight larger than that of the first substance 210 and the substrate 10 having the combining portion 240 disposed on its surface.

The detection device is a device that performs an arbitrary detection process using the sensor. Examples of the detection device include the SPR device, a control device of the SAW sensor, and the QCM measuring device. Preferably, the detection device is the control device of the SAW sensor. The SPR device, the control device of the SAW sensor, and the QCM measuring device serving as the detection device according to the disclosure may be an arbitrary device capable of performing measurement using the sensor, or a known device may be used without change or may be appropriately modified and then used.

Further, not a target substance, but a signal substance combined with the substrate surface or an aptamer disassociated from the substrate surface is detected by the sensor. For this reason, the detection device may perform a conversion process of converting a detection result obtained based on the signal substance or the like into a detection result of the target substance. For example, when a molecular weight of the target substance and a molecular weight of the signal substance are already known, if a result indicating that "the signal substance is "x" gram (or mol)," the result may be converted into a result indicting that the target substance is "y" gram (or mol)."

Detecting Portion of Sensor, Detection Method, Detection System, and Detection Device According to Second Embodiment The first embodiment has been described in connection with the example in which the change of the substrate surface caused by the second substance 220 having a molecular weight larger than that of the first substance 210 instead of the first substance 210 is detected. Here, the sensor according to the disclosure is not limited to this example.

FIG. 14 is a diagram for describing another embodiment of a sensor. In other words, for example, as illustrated in (1) of FIG. 14, an aptamer 300 having a molecular weight larger than that of a first substance 210 is combined with a combining portion 310 of a substrate surface in advance. Then, as illustrated in (2) of FIG. 14, when the first substance 210 is included in the analyte solution, the first substance 210 may be combined with the aptamer 300, the aptamer 300 may be disassociated from the combining portion 310 of the substrate surface, and the state change of the substrate surface caused by disassociation of the aptamer 300 may be detected.

The following description will proceed focusing on points different from the detecting portion of the sensor, the detection method, the detection system, and the detection device according to the first embodiment.

A sensor according to a second embodiment includes a substrate 10. The sensor further includes the combining portion 310 that is positioned on a surface of the substrate 10 and is being combined with the aptamer 300 that can be combined with the first substance 210. Here, the combining portion 310 can detect whether or not the first substance 210 is included.

For example, the sensor includes the combining portion 310 for the aptamer 300 including a combining part that is combined with the first substance 210. Further, for example, the sensor includes the substrate 10 in which the combining portion 310 that detects whether or not the first substance 210 is included in the analyte is disposed on its surface, and the aptamer 300 being combined with either of the first substance 210 and a combining portion 240 is combined with the combining portion 310.

In other words, similarly to the aptamer 230, the aptamer 300 includes two combining parts, and one of the combining parts is combined with the first substance 210, and the other is combined with the combining portion 310 of the substrate surface. In other words, the aptamer 300 includes a first combining part 231 that is combined with the first substance 210 and a combining part 321 that is combined with the combining portion 310. For example, when the combining portion 310 is formed of a nucleic acid, a nucleic acid having a base sequence complementary to the combining portion 310 is used as the combining part 321 of the aptamer 300 that is combined with the combining portion 310.

Further, a detection method according to the second embodiment includes a contact process of causing an analyte to come into contact with the surface of the substrate 10 of the sensor including the combining portion 310, the substrate 10 in which the combining portion 310 is disposed on its surface, and the aptamer 300 that is combined with the combining portion 310, includes the combining part that is combined with the first substance 210, and is combined with either of the first substance 210 and the combining portion 310. In other words, the detection method according to the second embodiment includes a contact process of causing the analyte solution to come into contact with the substrate surface of the sensor 100 in which the aptamer 300 that includes the combining part that is combined with the first substance 210 and is combined with either of the combining portion 310 of the substrate surface of the sensor and the first substance 210 is combined with the combining portion 310. The detection method according to the second embodiment further includes a detecting process of detecting whether or not the first substance 210 is included in the analyte by detecting the state change of the surface of the substrate 10 with which the analyte comes into contact by the contact process.

Further, the detection system according to the second embodiment include a sensor including the combining portion 310, the substrate 10 in which the combining portion 310 is disposed on its surface, and the aptamer 300 that is combined with the combining portion 310, includes the combining portion 310 that is combined with the first substance 210, and is combined with either of the first substance 210 and the combining portion 310. In other words, the detection system according to the second embodiment includes the sensor 100 in which the aptamer 300 that includes the first combining part 231 that is combined with the first substance 210 and is combined with either of the combining portion 310 of the substrate surface of the sensor 100 and the first substance 210 is combined with the combining portion 310. The detection system according to the second embodiment further includes a detection device that detects whether or not the first substance 210 is included in the analyte by detecting the state change of the surface of the substrate 10 when the analyte comes into contact with the surface of the substrate 10 of the sensor.

The detection device according to the second embodiment includes a detection control unit that detects whether or not the first substance 210 is included in the analyte by detecting the state change of the surface of the substrate 10 when the analyte comes into contact with the surface of the substrate 10 of the sensor including the combining portion 310, the substrate 10 in which the combining portion 310 is disposed on its surface, and the aptamer 300 that is combined with the combining portion 310, includes the combining portion 310 that is combined with the first substance 210, and is combined with either of the first substance 210 and the combining portion 310. In other words, the detection device according to the second embodiment includes a detection control unit that detects whether or not the first substance 210 is included in the analyte solution by detecting the state change of the substrate surface when the analyte solution comes into contact with the substrate surface of the sensor 100 in which the aptamer 300 that includes the combining part that is combined with the first substance 210 and is combined with either of the combining portion 310 of the substrate surface of the sensor 100 and the first substance 210 is combined with the combining portion 310.

Detecting Portion of Sensor, Detection Method, Detection System, and Detection Device According to Third Embodiment The above second embodiment has been described in connection with the example in which the aptamer 300 having a molecular weight larger than that of the first substance 210 is combined with the combining portion 310 of the substrate surface in advance, but the present invention is not limited to this example.

Figure 21:
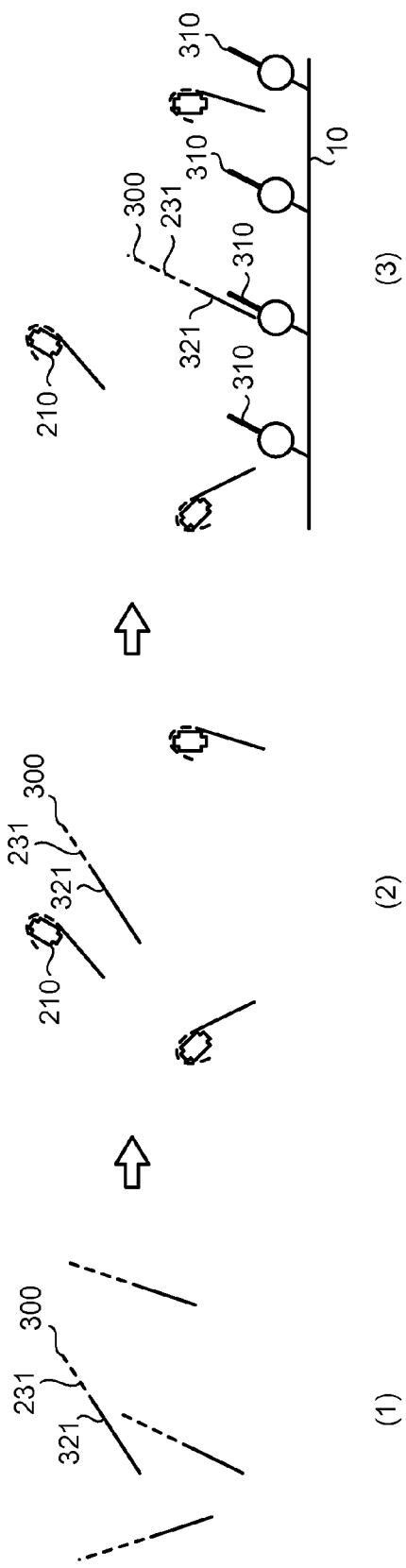
FIG. 21 is a diagram illustrating a third embodiment.

FIG. 21 is a diagram illustrating a third embodiment.

(1) of FIG. 21 illustrates a state in which there are a plurality of aptamers 300. (2) of FIG. 21 illustrates a state in which an analyte solution including a plurality of first substances 210 comes into contact with the aptamer 300. (3) of FIG. 21 illustrates a state in which the aptamer 300 coming into contact with an analyte solution including the first substance 210 comes into contact with a plurality of combining portions 310 positioned on a substrate 10.

In other words, for example, the combining portion 310 is not combined with the aptamer 300 in advance, and after the analyte solution comes into contact with the aptamer 300, the analyte solution comes into contact with the combining portion 310. Here, when the first substance 210 is included in the analyte solution, the first substance 210 is combined with the aptamer 300. As a result, among the aptamers 300 included in the analyte solution, the aptamer 300 that has not been combined with the first substance 210 is combined with the combining portion 310.

In the example illustrated in (1) of FIG. 21, there are four aptamers 300. Here, as illustrated in (2) of FIG. 21, when the first substance 210 is present in the analyte solution, the aptamer 300 is combined with the first substance 210. For example, in the example illustrated in (2) of FIG. 21, three of the four aptamers 300 are combined with the first substance 210. Thereafter, as illustrated in (3) of FIG. 21, in the combining portion 310 of the surface of the substrate 10, the aptamer 300 not being combined with the first substance 210 is combined with the combining portion 310, and the aptamer 300 being combined with the first substance 210 is not combined with the combining portion 310. In other words, for example, when the first substance 210 is not present in the analyte solution, each of the four aptamers 300 illustrated in (1) of FIG. 21 is combined with the combining portion 310, whereas, as illustrated in (2) and (3) of FIG. 21, when the first substance 210 is present in the analyte solution, the number of aptamers 300 to be combined with the combining portion 310 is reduced by the number of aptamers 300 that have been combined with the first substance 210.

Thus, when the first substance 210 is included in the analyte solution, the number of aptamers 300 to be combined with the combining portion 310 is smaller than when the first substance 210 is not included in the analyte solution. Similarly, as the number of first substances 210 included in the analyte solution increases, the number of aptamers 300 to be combined with the combining portion 310 decreases. In the third embodiment, it is possible to detect the state change of the surface of the substrate 10 caused by a combination of the aptamer 300 and the combining portion 310.

The third embodiment will be described in further detail. A sensor according to the third embodiment includes a substrate 10 and a combining portion 310 that is disposed on the substrate 10, and is combined with an aptamer 300 including a combining part that is combined with a first substance 210.

Here, in the third embodiment, it is detected whether or not the first substance 210 is included in the analyte solution by causing the analyte solution that comes into contact with the aptamer 300 to come into contact with the substrate 10 in which the combining portion 310 is disposed on its surface and detecting the state change of the surface of the substrate 10 coming into contact with the analyte solution. Specifically, based on the fact that when the first substance 210 is included in the analyte solution, a small number of aptamers 300 are combined with the combining portion 310 compared to when the first substance 210 is not included in the analyte solution, it is detected whether or not the first substance 210 is included in the analyte solution. Further, similarly, based on the fact that when the first substance 210 is included in the analyte solution, as the number of first substances 210 included in the analyte solution increases, the number of aptamers 300 to be combined with the combining portion 310 decreases, an amount of the first substances 210 included in the analyte solution is measured.

Here, for example, an amount of the aptamers 300 is more preferably equal to or larger than an upper limit of the number of moles in a concentration range of an analyte to be measured with respect to a concentration of an analyte, that is, the number of moles of the first substance 210 (to be combined with the aptamer 300). Further, the combining portion 310 is preferably immobilized to the substrate 10 in as high density as possible at which the aptamer 300 is combined with the combining portion 310 without being saturated when the first substance 210 is not combined with the aptamer 300. It is to make it possible to appropriately obtain a change in a state of the substrate surface according to a concentration of an analyte in a concentration range of an analyte to be measured.

As described above, in the third embodiment, even when a concentration of the first substance 210 is low, it is possible to obtain a signal for the concentration at an excellent SN.

Detecting Portion of Sensor, Detection Method, Detection System, and Detection Device According to Fourth Embodiment.

Further, for example, a relation between the aptamer and the second substance with respect to the combining portion of the substrate 10 may be changed.

Figure 22:
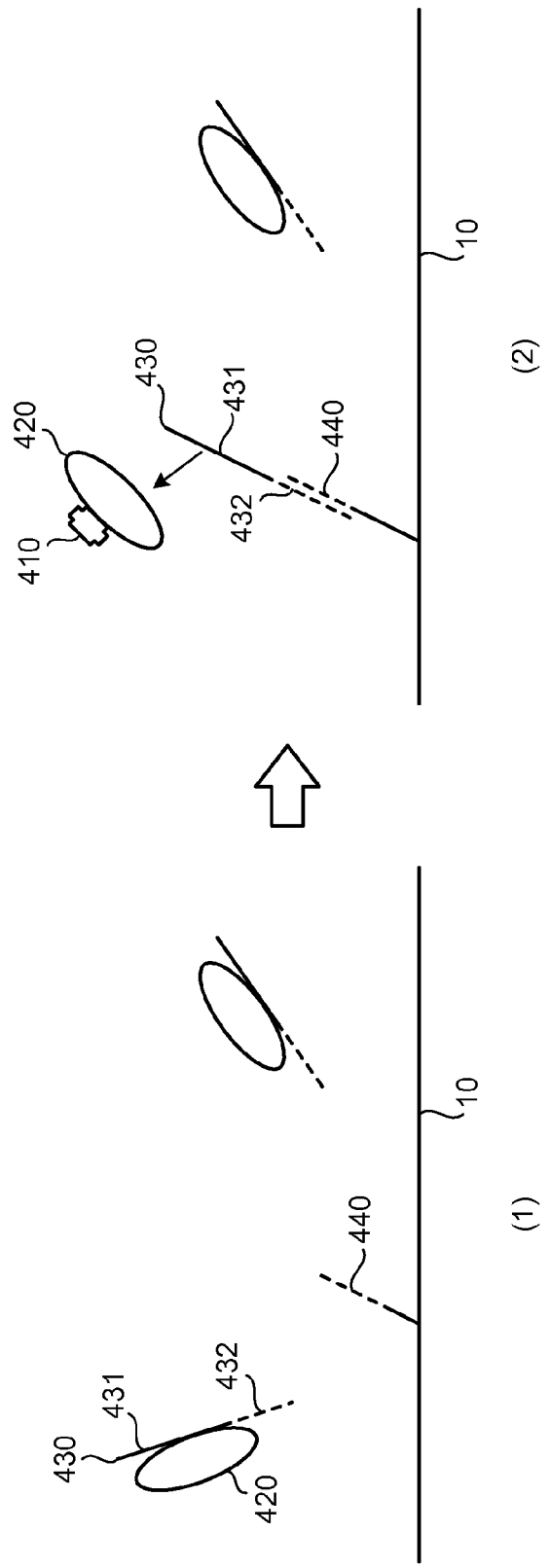
FIG. 22 is a diagram illustrating a fourth embodiment.

FIG. 22 is a diagram illustrating a fourth embodiment.

(1) of FIG. 22 illustrates a state in which in the analyte solution, there are an aptamer 430 and a second substance 420, but there is no first substance 410. (2) of FIG. 22 illustrates a state in which in the analyte solution of (1) of FIG. 22, there is the first substance 410 in addition to the aptamer 430 and the second substance 420. In other words, in the fourth embodiment, as illustrated in FIG. 22, the substrate 10 includes a combining portion 440 that is complementarily combined with the aptamer 430. The aptamer 430 includes a first combining part 431 that is combined with the second substance 420 and a second combining part 432 that is combined with the combining portion 440.

Here, the description will proceed with an example in which a first substance 410 is smaller in a molecular weight than the aptamer 430, and has a combining ability of combining with the second substance 420 stronger than a combining ability of combining with the aptamer 430. In this case, when the analyte solution including the aptamer 430 and the first substance 410 comes into contact with the surface of the substrate 10, the second substance 420 is disassociated from the aptamer 430, and combined with the first substance 410. Then, the aptamer 430 from which the second substance 420 has been disassociated is combined with the combining portion 440, and the state of the surface of the substrate 10 is changed.

For example, as illustrated in (1) of FIG. 22, when the first substance 210 is not present in the analyte solution, the aptamer 430 is designated such that the first combining part 431 of the aptamer 430 is combined with the second substance 420. On the other hand, as illustrated in (2) of FIG. 22, when the first substance 210 is present in the analyte solution, the aptamer 430 is designed such that the second substance 420 being combined with the aptamer 430 is combined with the first substance 410, and disassociated from the aptamer 430. Thereafter, the second combining part 432 of the aptamer 430 from which the second substance 420 has been disassociated is combined with the combining portion 440 disposed on the surface of the substrate 10.

In other words, in the fourth embodiment, when the first substance 410 is included in the analyte solution, the combining portion 440 is combined with the aptamer 430, and it is detected that the state of the surface of the substrate 10 is changed. In other words, the first substance 410 included in the analyte solution is detected by detecting the change in the state of the surface of the substrate 10 caused by a combination of the combining portion 440 and the aptamer 430.

Aptamer

The above embodiments have been described in connection with the example in which, for example, as illustrated in FIG. 12, the first combining part 231 for the first substance 210 and the second combining part 232 for the second substance 220 are formed at different positions in the aptamer 230. Here, the present invention is not limited to this example, and the first combining part 231 may overlap the second combining part 232 in whole or part. In other words, in the aptamer 230, at least a part of the first combining part 231 and at least a part of the second combining part 232 may be the same part. The aptamer 230 is preferentially combined with either of the first substance 210 and the combining portion 240.

Figure 23:
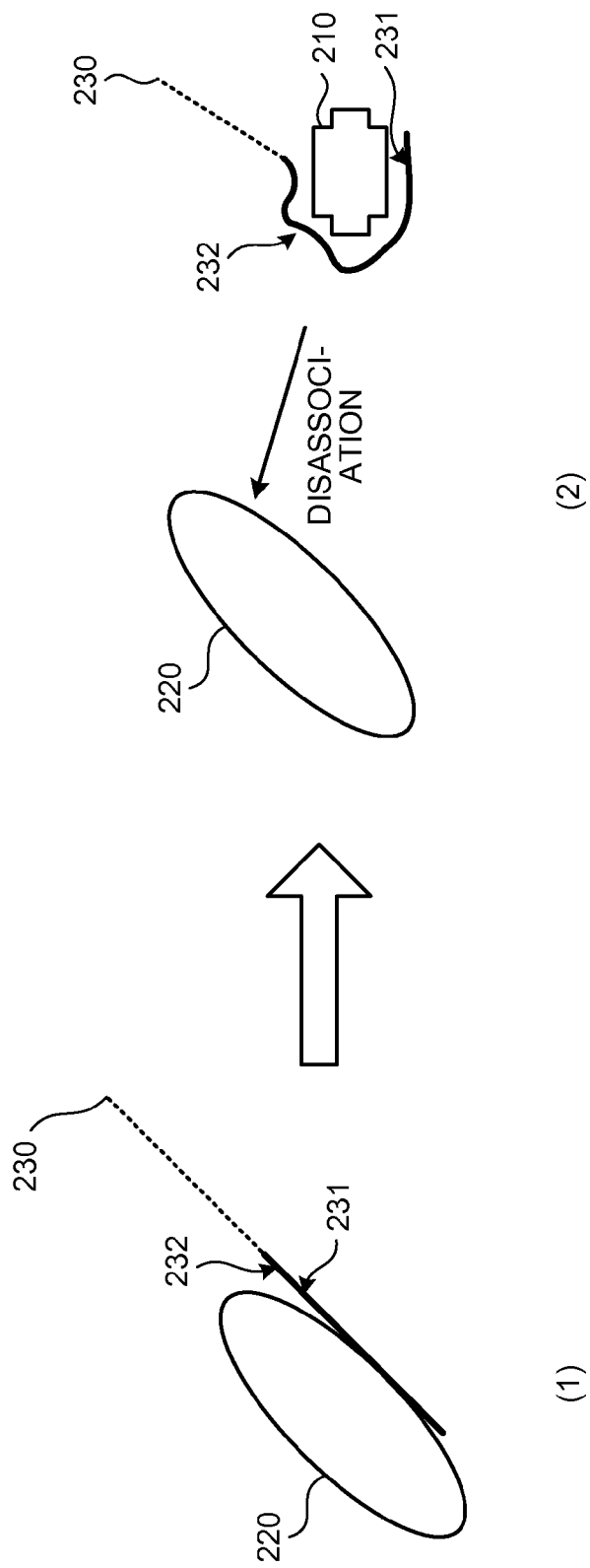
FIG. 23 is a diagram for describing an example of an embodiment of an aptamer according to the disclosure.

FIGS. 23 and 24 are diagrams for describing exemplary aptamers according to an embodiment of the disclosure. As illustrated in FIGS. 23 and 24, for example, the first combining part 231 may overlap the second combining part 232 in whole or part, or both the first substance 210 and the second substance 220 may be combined with the same part. In the example illustrated in FIG. 23, in the aptamer 230, the second substance 220 is combined with one surface of a solid line part, and the first substance 210 is combined with the other surface of the solid line part. In other words, the solid line part of FIG. 23 includes the first combining part and the second combining part. Further, in the example illustrated in FIG. 24, the first combining part 231 partially overlaps the second combining part 232. In other words, as illustrated in FIG. 24, the first combining part 231 is indicated by a dotted line, the second combining part 232 is indicated by a solid line, and the first combining part 231 partially overlaps the second combining part 232. Thus, the aptamers 230 of FIGS. 23 and 24 have the same function as that of the aptamer 230 of FIG. 12.

EXAMPLES

Hereinafter, examples will be described in further detail in connection with an example in which in the sensor, the detection method, the detection system, and the detection device according to the disclosure, an ATP is used as the first substance, and the SPR device is used as a measuring device. Here, the sensor, the detection method, the detection system, and the detection device according to the disclosure are not limited to the following examples.

In the following, a sensor chip SA (GE Healthcare) is used as a sensor. The sensor chip SA is a chip used for SPR measurement by a BIACORE-X system. In the sensor chip SA, streptavidin is immobilized onto a substrate in advance through carboxymethyl dextran. The following description will proceed with an example of the aptamer 230 using an ATP as the first substance 210. Hereinafter, the aptamer 230 using an ATP as the first substance 210 is referred to as an "ATP aptamer."

Examples 1 to 9

In Examples 1 to 9, as will be described below in detail, an ATP aptamer complementary strand DNA mixed liquid was prepared. Further, a biotin DNA solution was prepared. Thereafter, immobilization of biotin DNA onto the sensor chip SA and checking of the immobilization were performed, and SPR measuring was performed.

Preparation of ATP Aptamer Complementary Strand DNA Mixed Liquid

A mixed liquid of an ATP aptamer having a base sequence described as a sequence number 1 in the sequence listing and one of DNAs "A" to "C" having base sequences described as sequence numbers 3 to 5 in the sequence listing was prepared. The ATP aptamer and the DNAs "A" to "C" were obtained by custom synthesis (Gene Design Inc.). Hereinafter, the DNAs "A" to "C" are also referred to as complementary strand DNAs "A" to "C," respectively.

Sequence number 1:
5'-ACCTGGGGGAGTATTGCGGAGGAAGGT-3'

Sequence number 3:
5'-TTTTTTTTTTTTTTTTTTTTTTTTTTACCTTCCTCC-3'

Sequence number 4:
5'-TTTTTTTTTTTTTTTTTTTTTTTTTTACCTTCCTCCGC-3'

Sequence number 5:
5'-TTTTTTTTTTTTTTTTTTTTTTTTTTACCTTCCTCCGCAA-3'

Specifically, first, an ATP aptamer 80 μl of 10 μM was mixed with a complementary strand DNA 40 μl to 10 μM. Then, annealing of the ATP aptamer and the complementary strand DNA was performed such that the mixed liquid of the ATP aptamer and the complementary strand DNA[x] was heated for one minute at a temperature of 95°, heated for one minutes at a temperature of 75°, and then placed for 30 minutes at a room temperature.

Here, as illustrated in FIG. 15, the base sequence of the ATP aptamer and the base sequence of the complementary strand DNA "A" are complementary to each other from the 3 terminal side to the 10 base sequence. FIG. 15 is a diagram for describing a base sequence relation between the ATP aptamer and the complementary strand DNA "A." Similarly, the base sequence of the ATP aptamer and the base sequence of the complementary strand DNA "B" are complementary to each other from the 3 terminal side to the 12 base sequence. Further, the base sequence of the ATP aptamer and the base sequence of the complementary strand DNA "C" are complementary to each other from the 3 terminal side to the 14 base sequence. As described above, the complementary strand DNAs "A" to "C" differ in combination force with the ATP aptamer. Specifically, the combination force increase in the order of the complementary strands DNAs "C," "B," and "A."

Preparation of Biotin DNA Solution

A biotin DNA solution 200 µl was prepared by mixing a biotin DNA 1 µl of 10 mM with a HBS-N buffer (BIACORE) 199 µl. The biotin DNA has a base sequence described as the sequence number 2 in the sequence listing, and has biotin added to the 5 terminal side of the base sequence. A final concentration of the biotin DNA was 5 µM. The biotin DNA was obtained by custom synthesis (Gene Design Inc.).

Sequence number 2: 5'-GGAGGAAGGT-3'

Immobilization of Biotin DNA to Sensor Chip and Checking of Immobilization

The biotin DNA was immobilized to the sensor chip SA using strong affinity between streptavidin and biotin. Further, SPR measuring was performed using the BIACORE-X (GE Healthcare Japan Corporation), and the immobilization of the biotin DNA was checked. The following condition was used when the measuring was performed using the BIACORE-X system.

Running buffer: HBS-N buffer (BIACORE)
Velocity: 5 µl/min
Temperature: 25°

Specifically, the biotin DNA solution 50 µl was injected into the flow cell of the BIACORE-X system in which the sensor chip SA is set, and then the biotin DNA solution 30 µl was further injected. Thereafter, in order to flush the biotin DNA non-specifically absorbed to the sensor chip SA, NaOH of 10 mM was injected into the flow cell appropriately, and the sensor chip SA was cleaned.

Figure 16:
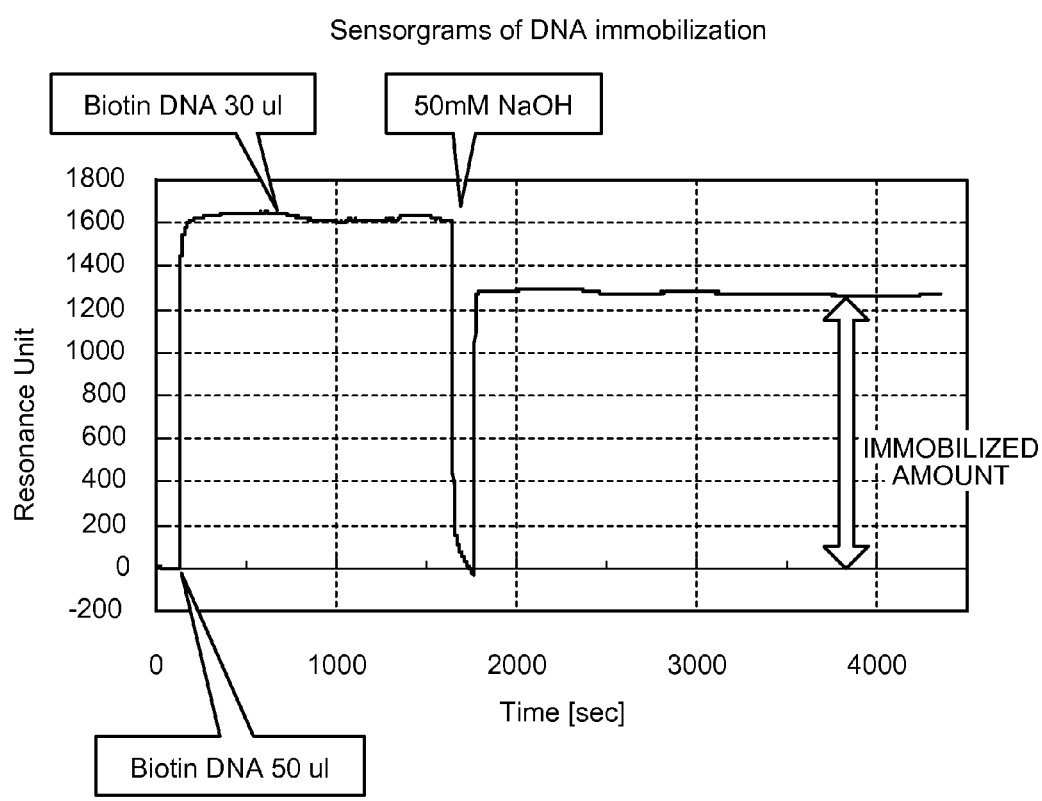
FIG. 16 is a diagram illustrating a sensorgram obtained in a BIACORE-X system.

FIG. 16 is a diagram illustrating a sensorgram obtained in the BIACORE-X system. In the sensorgram, a horizontal axis indicates a time axis, and a vertical axis indicates a mass change. A resonance unit (RU) that is a unit used in the BIACORE-X system was used as a unit of the vertical axis. 1 RU indicates that there was a mass change of 1 pg per 1 mm². In FIG. 16, for convenience of description, a timing at which the biotin DNA solution 50 µl was putted into, a timing at which the biotin DNA solution 30 µl was further putted into, and a timing at which NaOH of 50 mM was injected are illustrated.

In the sensorgram, an amount of increase in an RU between before the biotin DNA is injected and after cleaning by NaOH of 50 mM was performed is indicated by an immobilized amount of the biotin DNA. In the example illustrated in FIG. 16, ΔRU was about "1270," and the immobilized amount of the biotin DNA was about 1270 pg/mm².

SPR Measurement

Figure 19:
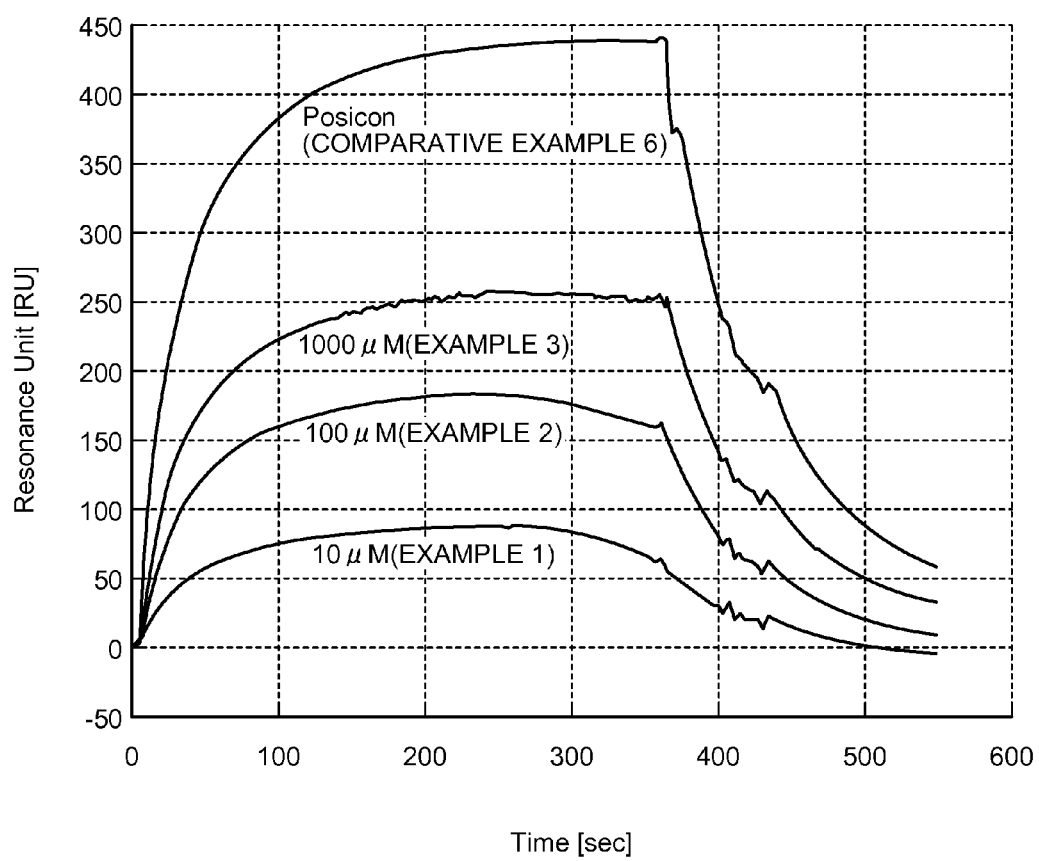
FIG. 19 is a diagram illustrating sensorgrams obtained in Examples 1 to 3 and Comparative Example 6 serving as positive control in Table 1.
Figure 20:
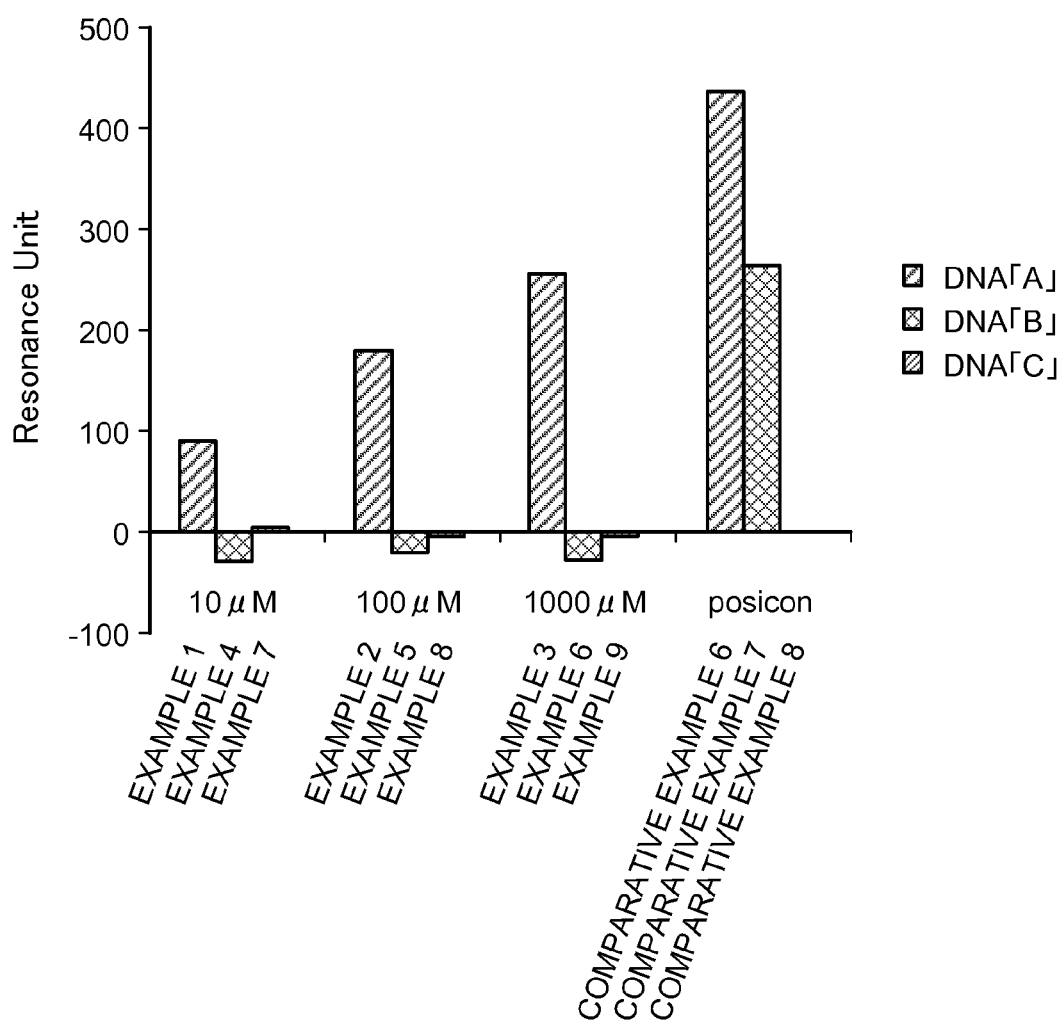
FIG. 20 is a diagram illustrating ΔRU in Examples 1 to 9 and Comparative Examples 6 to 8 serving as positive control in Table 1.

The SPR measuring was performed using the sensor chip SA to which the biotin DNA is immobilized. Specifically, as shown in Examples 1 to 9 of Table 1, the analyte solution in which the concentration of the ATP is [y] was prepared by mixing the ATP aptamer complementary strand DNA mixed liquid prepared using the complementary strand DNA[x] with the ATP. Then, the prepared analyte solution 35 µl was injected into the flow cell of the BIACORE-X system. The following condition was used when the measuring was performed using the BIACORE-X system. The measurement results are illustrated in FIGS. 19 and 20.

Running buffer: 50 mM Tris (Tris-(hydroxymethyl)aminomethane), 500 mM NaCl, and 5 mM MgCl₂
Velocity: 5 µl/min
Temperature: 25°

TABLE 1

| |
|---|
| Comparative Example 1 |
| Comparative Example 2 |
| Comparative Example 3 |
| Comparative Example 4 |
| Comparative Example 5 |
| Comparative Example 6 |
| Comparative Example 7 |
| Comparative Example 8 |
| Example 1 |
| Example 2 |
| Example 3 |
| Example 4 |
| Example 5 |
| Example 6 |
| Example 7 |
| Example 8 |
| Example 9 |
| ATP solution |
| complementary strand DNA solution |
| ATP aptamer complementary strand DNA mixed liquid |
| complementary strand DNA[x] |
| complementary strand A |
| complementary strand B |
| complementary strand C |
| complementary strand A |
| complementary strand A |
| complementary strand A |
| complementary strand B |
| complementary strand B |
| complementary strand B |
| complementary strand C |
| complementary strand C |
| complementary strand C |
| ATP concentration [y] |

Comparative Examples 1 to 5

In Comparative Examples 1 to 5, as will be described below in detail, a biotin ATP aptamer solution was prepared. Thereafter, immobilization of the biotin ATP aptamer onto the sensor chip SA and checking of the immobilization were performed, and SPR measuring was performed.

In other words, in Comparative Examples 1 to 5, unlike Examples 1 to 9, the biotin ATP aptamer was immobilized to the sensor chip SA instead of the biotin DNA. As a result, in Examples 1 to 9, the complementary strand DNA is combined with the biotin DNA immobilized onto the sensor chip SA, whereas in Comparative Examples 1 to 5, the ATP is combined with the biotin ATP aptamer immobilized to the sensor chip SA. Further, the biotin ATP aptamer has the base sequence described as the sequence number 1 in the sequence listing, and has biotin added to the 5 terminal side of the base sequence. The biotin ATP aptamer was obtained by custom synthesis (Gene Design Inc.).

Preparation of Biotin ATP Aptamer Solution

A biotin ATP aptamer solution 200 µl was prepared by mixing the biotin ATP aptamer 1 µl of 10 mM with the HBS-N buffer (BIACORE) 199 µl. In the prepared biotin ATP aptamer solution, the final concentration of the biotin ATP aptamer was 5 µM.

Immobilization of Biotin ATP Aptamer onto Sensor Chip and Checking of Immobilization In the BIACORE-X system, the biotin ATP aptamer was immobilized to the sensor chip SA using strong affinity between streptavidin and biotin. Further, SPR measuring was performed using the BIACORE-X, and the immobilization of the biotin ATP aptamer was checked based on the sensorgram obtained as a measurement result. The following condition was used when the measuring was performed using the BIACORE-X system, similarly to the checking of the immobilization of the biotin DNA in Examples 1 to 9.

Running buffer: HBS-N buffer (BIACORE)
Velocity: 5 µl/min
Temperature: 25°

Specifically, the biotin ATP aptamer solution 50 µl was injected into the flow cell of the BIACORE-X system in which the sensor chip SA is set, and then the biotin ATP aptamer solution 30 µl was further injected. Thereafter, in order to flush the biotin ATP aptamer absorbed to the sensor chip SA regardless of a covalent bond, NaOH of 50 mM was injected into the flow cell, and the sensor chip SA was cleaned.

Figure 17:
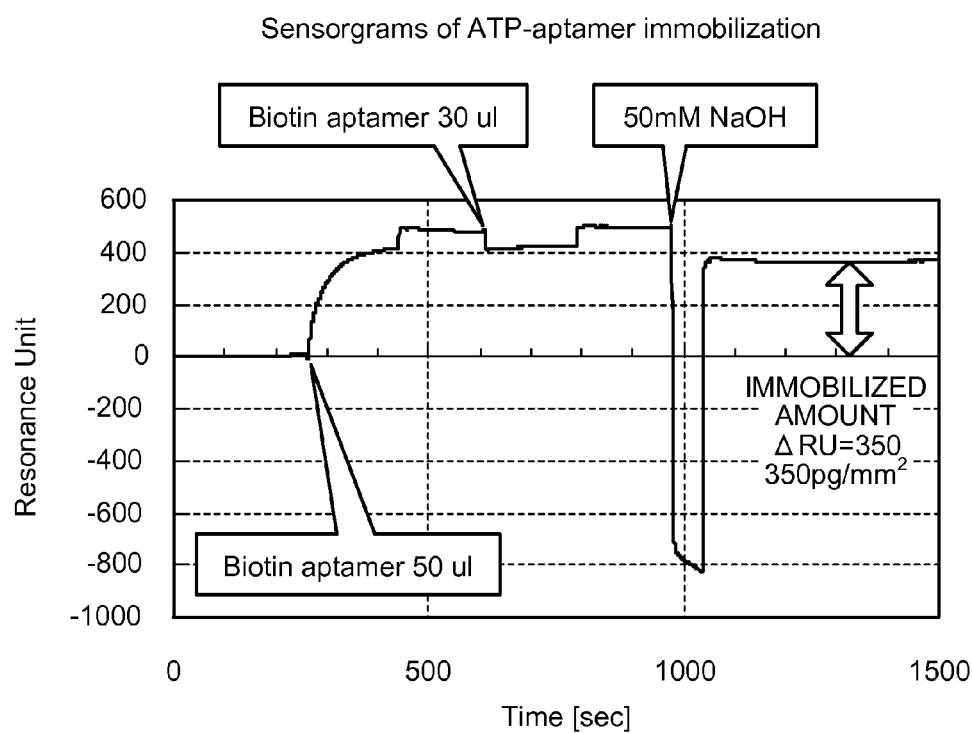
FIG. 17 is a diagram illustrating a sensorgram obtained in a BIACORE-X system.

FIG. 17 is a diagram illustrating a sensorgram obtained in the BIACORE-X system. In the sensorgram, a horizontal axis indicates a time axis, and a vertical axis indicates a mass change. An RU that is a unit used in the BIACORE-X system was used as a unit of the vertical axis. 1 RU indicates that there was a mass change of 1 pg per 1 mm$^2$. In FIG. 17, for convenience of description, a timing at which the biotin ATP aptamer solution 50 µl was putted into, a timing at which the biotin ATP aptamer solution 30 µl was putted into, and a timing at which NaOH of 50 mM was injected are illustrated.

In the sensorgram, an amount of increase in an RU between before the biotin ATP aptamer solution is injected and after cleaning by NaOH of 50 mM was performed is indicated by an immobilized amount of the biotin ATP aptamer solution. In the example illustrated in FIG. 17, ΔRU was about "350," and the immobilized amount of the biotin DNA was about 350 pg/mm$^2$.

ATP Measurement Process

Figure 18:
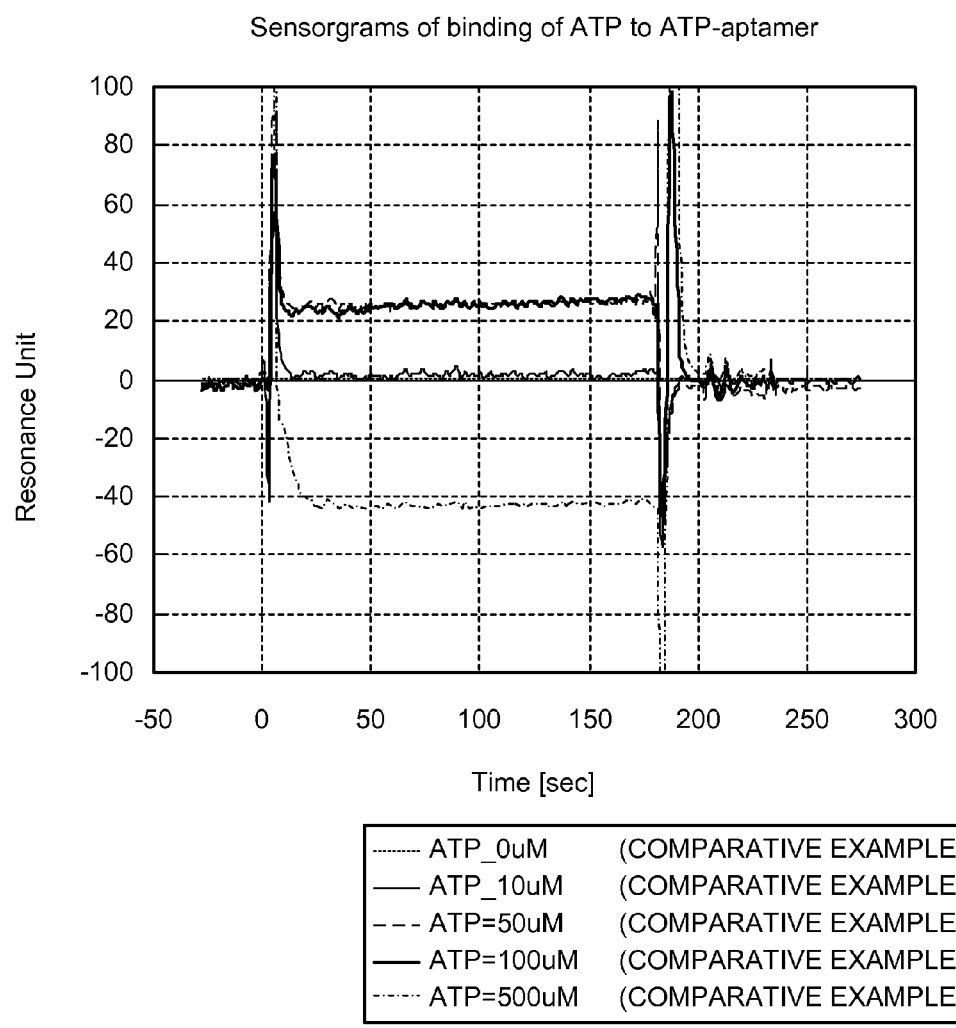
FIG. 18 is a diagram illustrating sensorgrams obtained in Comparative Examples 1 to 5 in Table 1.

As shown in Comparative Examples 1 to 5 of Table 1, an ATP solution in which the concentration of the ATP is [y] was prepared, and the prepared ATP solution 35 µl was injected into the flow cell of the BIACORE-X system in which the sensor chip SA to which the biotin ATP aptamer is immobilized is set. The following condition was used when the measuring was performed using the BIACORE-X system, similarly to the ATP measurement process in Examples 1 to 9. The measurement results are illustrated in FIG. 18.

Running buffer: 50 mM Tris (Tris-(hydroxymethyl)aminomethane), 500 mM NaCl, and 5 mM MgCl$_2$
Velocity: 5 µl/min
Temperature: 25°

Comparative Example 6 to 8

In Comparative Examples 6 to 8, as will be described below in detail, unlike Examples 1 to 9, a complementary strand DNA solution including only a complementary strand DNA[x] of 5 mM was injected at the time of SPR measuring. It was used as the analyte solution.

In other words, in Examples 1 to 9, the ATP aptamer and the complementary strand DNA was annealed, the liquid mixed with the ATP was prepared, and then the ATP aptamer and the complementary strand DNA were injected, whereas in Comparative Examples 6 to 8, only the complementary strand DNA was injected. Comparative Examples 6 to 8 correspond to positive control of Examples 1 to 9.

Specifically, as shown in Comparative Examples 6 to 8 of Table 1, a complementary strand DNA solution including a complementary strand DNA[x] of 5 mM was prepared. Then, the prepared complementary strand DNA solution 35 µl was injected into the flow cell of the BIACORE-X system in which the sensor chip SA to which the biotin DNA is immobilized is set. The measurement condition used in the BIACORE-X system is as follows, similarly to the SPR measuring in Examples 1 to 9. The measurement results are illustrated in FIGS. 19 and 20.

Running buffer: 50 mM Tris (Tris-(hydroxymethyl)aminomethane), 500 mM NaCl, and 5 mM MgCl$_2$
Velocity: 5 µl/min
Temperature: 25°

Measurement Results of SPR Measurement

FIG. 18 is a diagram illustrating sensorgrams obtained in Comparative Examples 1 to 5 in Table 1. In other words, the measurement results when the biotin ATP aptamer was immobilized to the sensor chip SA, and then the ATP solution was injected are illustrated. As illustrated in FIG. 18, a weight change caused by combination of the biotin ATP aptamer immobilized to the sensor chip SA and the ATP was not measured.

FIG. 19 is a diagram illustrating sensorgrams obtained in Examples 1 to 3 and Comparative Example 6 serving as the positive control in Table 1. In other words, the measurement results when the complementary strand DNA "A" is used as the complementary strand DNA[x] are illustrated. As illustrated in FIG. 19, a weight change caused by a combination of the biotin DNA immobilized to the sensor chip SA and the complementary strand DNA disassociated as the ATP is combined with the ATP aptamer when the complementary strand DNA "A" is used was measured.

FIG. 20 is a diagram illustrating ΔRU in Examples 1 to 9 and Comparative Examples 6 to 8 serving as the positive control in Table 1. In other words, the measurement results when the complementary strand DNAs "A," "B," and "C" are used as the complementary strand DNA[x] are illustrated. As illustrated in FIG. 20, for the complementary strand DNA "A," a weight change according to a change in a concentration of the ATP was detected, but for the complementary strand DNAs "B" and "C," a weight change was not detected.

In other words, as illustrated in FIGS. 18 to 20, it is possible to detect a small molecule having a relatively small molecular weight by detecting the change of the substrate surface caused by a combination with the complementary strand DNA other than the ATP. Further, as illustrated in FIGS. 19 and 20, an amount of an ATP serving as a target substance and a change amount of the detected state change of the substrate surface were found to have a proportional relation. As a result, as illustrated in FIGS. 19 and 20, it is possible to measure an amount of a small molecule serving as a target substance.

REFERENCE SIGNS LIST

1 FIRST COVER MEMBER
2 SECOND COVER MEMBER
3 DETECTING ELEMENT
4 CONCAVE PORTION FORMING THROUGH HOLE
5 CONCAVE PORTION
8 NOTCH
10 SUBSTRATE

| | |
|---|---|
| 11 FIRST IDT ELECTRODE | 220 SECOND SUBSTANCE |
| 12 SECOND IDT ELECTRODE | 230 APTAMER |
| 13 DETECTING PORTION | 231 FIRST COMBINING PART |
| 14 INLET | 232 SECOND COMBINING PART |
| 15 GROOVE PORTION | 240 COMBINING PORTION |
| 100 SENSOR | 300 APTAMER |
| 210 FIRST SUBSTANCE | 310 COMBINING PORTION |

The invention claimed is:

1. A sensor, comprising:
   a substrate,
   at least one of an aptamer, a protein and an antibody,
   a second substance having a molecular weight larger than a molecular weight of a first substance, and
   a combining portion disposed on a surface of the substrate, wherein the combining portion is not initially combined with the second substance, wherein the combining portion is capable of combining with the second substance,
   wherein the combining portion is disposed on the surface of the substrate for detecting whether or not the first substance is included in an analyte having come into contact with both at least one of an aptamer, a protein, and an antibody and the second substance,
   wherein the at least one of an aptamer, a protein, and an antibody includes a first combining part for the first substance and a second combining part for the second substance and is capable of being combined with either of the first substance and the second substance, and
   wherein when the first substance is included in the analyte it combines to the at least one of an aptamer, a protein, and an antibody, and the second substance combines with the combining portion disposed on the surface of the substrate.

2. The sensor according to claim 1,
   wherein in the aptamer, at least a part of the first combining part and at least a part of the second combining part are a same part.

3. The sensor according to claim 1,
   wherein the at least one of an aptamer, a protein, and an antibody is preferentially combined with either of the first substance and the combining portion.

4. The sensor according to claim 1,
   wherein a first free energy change calculated from a dissociation constant of the first substance and the at least one of an aptamer, a protein, and an antibody is smaller than a second free energy change associated with a combination of the at least one of an aptamer, a protein, and an antibody and the second substance, and a third free energy change associated with a combination of the second substance and the combining portion is larger than the second free energy change.

5. The sensor according to claim 4,
   wherein each of the at least one of an aptamer, a protein, and an antibody and the combining portion has a base sequence,
   the base sequence of the at least one of an aptamer, a protein, and an antibody has a part complementary to a first part of a base sequence of the second substance, and the base sequence of the combining portion has a part complementary to a second part of the base sequence of the second substance,
   the second free energy change is free energy change associated with a combination of the first part of the base sequence of the second substance and the complementary part of the base sequence of at least one of an aptamer, a protein, and an antibody,
   the third free energy change is free energy change associated with a combination of the second part of the base sequence of the second substance and the complementary part of the base sequence of the combining portion, and
   a base type and a base number of a base sequence complementary between the at least one of an aptamer, a protein, and an antibody and the second substance and a base type and a base number of a base sequence complementary between the combining portion and the second substance have values satisfying a magnitude relation among the first free energy change, the second free energy change, and the third free energy change.

6. The sensor according to claim 1, further comprising:
   a first cover member in which the substrate is positioned on an upper surface; and
   a second cover member bonded to the first cover member,
   wherein at least one of the first cover member and the second cover member comprises an inlet into which the analyte flows, and
   a flow channel extending from the inlet to at least the surface of the substrate is formed between the first cover member and the second cover member.

7. The sensor according to claim 6,
   wherein the flow channel includes a groove portion formed on a surface of at least one of the first cover member and the second cover member.

8. The sensor according to claim 7,
   wherein the first cover member comprises a concave portion accommodating at least a part of the substrate on the upper surface, and
   the second cover member comprises the groove portion.

9. The sensor according to claim 7,
   wherein the at least one of an aptamer, a protein, and an antibody and the second substance are each attached to the groove portion, and
   the combining portion is configured to detect the first substance from the analyte that has come into contact with the at least one of an aptamer, a protein, and an antibody and the second substance attached to the groove portion.

10. The sensor according to claim 7,
    wherein the at least one of an aptamer, a protein, and an antibody is immobilized to the groove portion, and combined with the second substance, and
    the combining portion is configured to detect the first substance from the analyte that has come into contact with the at least one of an aptamer, a protein, and an antibody.

11. The sensor according to claim 10,
    wherein the at least one of an aptamer, a protein, and an antibody being combined with the second substance is chemically combined with a surface substance of the groove portion.

12. The sensor according to claim 1, further comprising:
    a first InterDigital Transducer (IDT) electrode that is positioned on the surface of the substrate and is configured to generate an acoustic wave propagating toward a detecting portion on which the combining portion is positioned on the surface of the substrate; and
    a second IDT electrode that is positioned on the surface of the substrate, and is configured to receive the acoustic wave having passed through the detecting portion.

13. The sensor according to claim 12, further comprising:
    a first bonding member that is bonded to an upper surface of the substrate, and constitutes a first oscillation space hermetically-sealed between the first bonding member and the upper surface of the substrate; and
    a second bonding member that is bonded to the upper surface of the substrate, and constitutes a second oscillation space hermetically-sealed between the second bonding member and the upper surface of the substrate,
    wherein the first oscillation space is positioned on the first IDT electrode, and the second oscillation space is positioned on the second IDT electrode.

14. The sensor according to claim 1,
wherein at least one of the at least one of an aptamer, a protein, and an antibody and the analyte is positioned away from the combining portion.
15. The sensor according to claim 14,
wherein at least one of the at least one of an aptamer, a protein, and an antibody and the analyte is positioned in the flow channel.
16. The sensor according to claim 12,
wherein at least one of the at least one of an aptamer, a protein, and an antibody and the analyte is positioned in the detecting portion.

* * * * *

SEQUENCE LISTING

<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: Sequence of ATP aptamer

<400> SEQUENCE: 1
acctggggga gtattgcgga ggaaggt        27

<210> SEQ ID NO 2
<211> LENGTH: 10
<212> TYPE: DNA
<213> ORGANISM: Artificial Sequence
<220> FEATURE:
<223> OTHER INFORMATION: DNA fragments for sensor

<400> SEQUENCE: 2
ggaggaaggt        10

<210> SEQ ID NO 3
<211> LENGTH: 40
<212> TYPE: DNA
<213> ORGANISM: Artificial Sequence
<220> FEATURE:
<223> OTHER INFORMATION: DNA fragments A

<400> SEQUENCE: 3
tttttttttt tttttttttt tttttttttt accttcctcc        40

<210> SEQ ID NO 4
<211> LENGTH: 42
<212> TYPE: DNA
<213> ORGANISM: Artificial Sequence
<220> FEATURE:
<223> OTHER INFORMATION: DNA fragments B

<400> SEQUENCE: 4
tttttttttt tttttttttt tttttttttt accttcctcc gc        42

<210> SEQ ID NO 5
<211> LENGTH: 44
<212> TYPE: DNA
<213> ORGANISM: Artificial Sequence
<220> FEATURE:
<223> OTHER INFORMATION: DNA fragments C

<400> SEQUENCE: 5
tttttttttt tttttttttt tttttttttt accttcctcc gcaa        44